(12) United States Patent
Srivastava et al.

(10) Patent No.: US 6,828,429 B1
(45) Date of Patent: Dec. 7, 2004

(54) PROSTATE-SPECIFIC GENE, PCGEM1, AND THE METHODS OF USING PCGEM1 TO DETECT, TREAT, AND PREVENT PROSTATE CANCER

(75) Inventors: Shiv Srivastava, Potomac, MD (US); Vasantha Srikantan, Rockville, MD (US); Zhiqiang Zou, Gaithersburg, MD (US); Judd W. Moul, Bethesda, MD (US)

(73) Assignee: Henry M. Jackson Foundation for the Advancement of Military Medicine, Rockville, MD (US)

( * ) Notice: Subject to any disclaimer, the term of this patent is extended or adjusted under 35 U.S.C. 154(b) by 0 days.

(21) Appl. No.: 09/534,072

(22) Filed: Mar. 24, 2000

Related U.S. Application Data

(60) Provisional application No. 60/126,469, filed on Mar. 26, 1999.

(51) Int. Cl.$^7$ ............................................. C07H 21/04
(52) U.S. Cl. ................... 536/23.1; 435/320.1; 435/325; 536/24.1
(58) Field of Search .............................. 536/23.1, 24.1, 536/24.3; 435/320.1, 325

(56) References Cited

FOREIGN PATENT DOCUMENTS

| WO | WO 95/19434 | 7/1995 |
|----|-------------|--------|
| WO | WO 99/00498 | 1/1999 |

OTHER PUBLICATIONS

GenBank, Accession No. AC013401, GI:6289254, 163807 bp DNA, Nov. 9, 1999.
GenBank, Accession No. AC013401, GI:8050939, 170695 bp DNA, May 24, 2000.
GenBank, Accession No. AC013401, GI:8099084, 172760 bp DNA, May 26, 2000.
GenBank, Accession No. AC013401, GI:8569780, 169700 bp DNA, Jul. 7, 2000.
Srikantan et al., "PCGEM1, a Prostate–Specific Gene, Is Overexposed in Prostate Cancer", *Proc. Nat'l. Acad. Sci.*, vol. 97, No. 22, pp. 12216–12221 (Oct. 24, 2000).
Srikantan et al., "Identification of Prostate Cancer Associated Novel Gene Expression Alterations", *Proc. American Assoc. Cancer Research*, vol. 39, p. 362 (Mar. 1998).
Srikantan et al., "Identification of Prostate Cancer Associated Novel Gene Expression Alterations", *USUHS Research Day–Graduate Student Colloquium*, p. 164 (Apr. 1–2, 1998).
Srikantan et al., "Identification of Prostate Cancer Associated Novel Gene Expression Alterations", *J. Urology*, AUA 93$^{rd}$ Annual Meeting, p. 40 (May 30–Jun. 4, 1998).
Srikantan et al., "Structure and Expression of a Novel Prostate Specific Gene:PC–GEM1," *Proc. American Assoc. Cancer Research Annual*, XP000929230, vol. 40, p. 37 (Mar. 1999).
Bussemakers et al., "A New Prostate–Specific Marker, Strongly Overexpressed In Prostatic Tumors," *Urological Research*, XP002074305, vol. 25, No. 1, p. 76 (Feb. 1997).
Wang et al., "Genes Regulated by Androgen in the Rat Ventral Prostate," *Proc. Nat'l. Acad. Sci., U.S.A.*, vol. 94, pp. 12999–13004 (Nov. 1997).

*Primary Examiner*—Anthony C. Caputa
*Assistant Examiner*—Stephen L. Rawlings
(74) *Attorney, Agent, or Firm*—Finnegan, Henderson, Farabow, Garrett & Dunner, L.L.P.

(57) ABSTRACT

A nucleic acid sequence that exhibits prostate-specific expression and over-expression in tumor cells is disclosed. The sequence and fragments thereof are useful for detecting, diagnosing, preventing, and treating prostate cancer and other prostate related diseases. The sequence is also useful for measuring hormone responsiveness of prostate cancer cells.

8 Claims, 21 Drawing Sheets

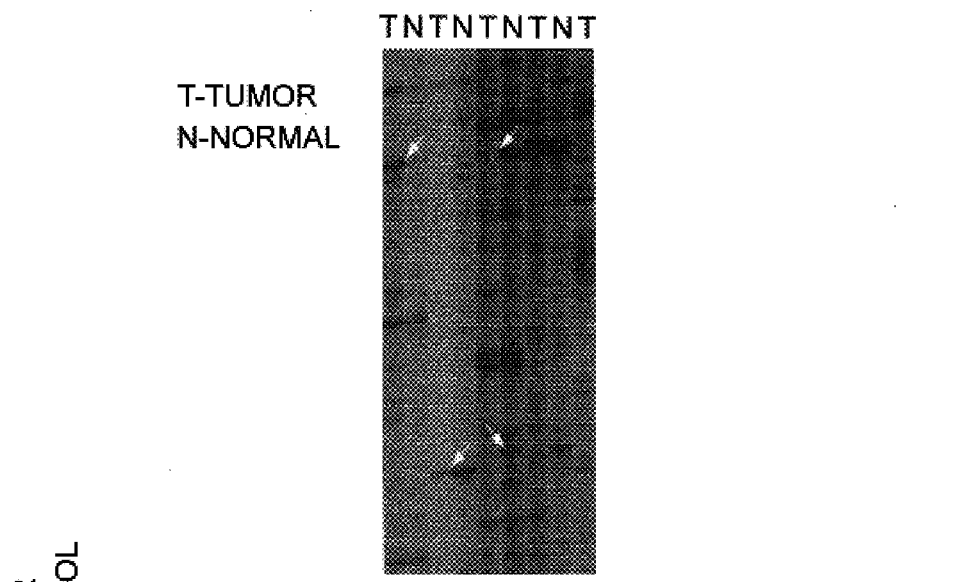
FIG. 2
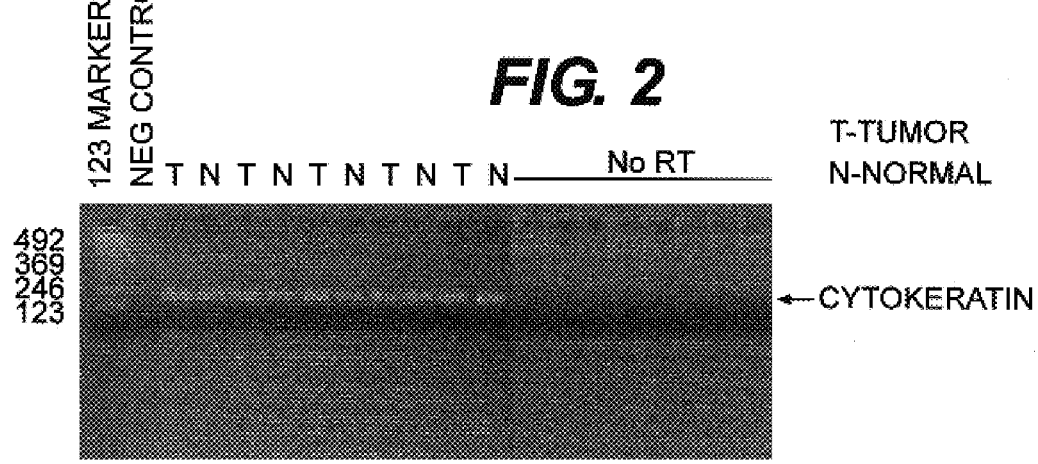
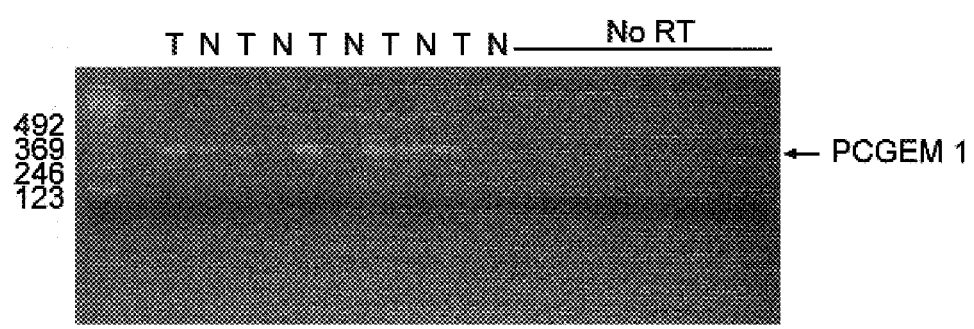
FIG. 3

FIG. 6B cDNA sequence of PCGEM1 Seq.ID No .1

```
AAGGCACTCT GGCACCCAGT TTTGGAACTG CAGTTTTAAA AGTCATAAAT TGAATGAAAA TGATAGCAAA    70
GGTGGAGGTT TTTAAAGAGC TATTTATAGG TCCCTGGACA GCATCTTTTT TCAATTAGGC AGCAACCTTT   140
TTGCCCTATG CCGTAACCTG TGTCTGCAAC TTCCTCTAAT TGGGAAATAG TTAAGCAGAT TCATAGAGCT   210
GAATGATAAA ATTGTACTAC GAGATGCACT GGGACTCAAC GTGACCTTAT CAAGTGAGCA GGCTTGGTGC   280
ATTTGACACT TCATGATATC AGCCAAAGTG GAACTAAAAA CAGCTCCTGG AAGAGGACTA TGACATCATC   350
AGGTTGGGAG TCTCCAGGGA CAGCGGACCC TTTGGAAAAG GACTAGAAAG TGTGAAATCT ATTAGTCTTC   420

GATATGAAAT TCTCTGTCTC TGTAAAAGCA TTTCATATTT ACAAGACACA GGCCTACTCC TAGGGCAGCA   490
AAAAGTGGCA ACAGGCAAGC AGAGGGAAAA GAGATCATGA GGCATTTCAG AGTGCACTGT CTTTTCATAT   560
ATTTCTCAAT GCCGTATGTT TGGTTTTATT TTGGCCAAGC ATAACAATCT GCTCAAGAAA AAAAAATCTG   630
GAGAAAACAA AGGTGCCTTT GCCAATGTTA TGTTTCTTTT TGACAAGCCC TGAGATTTCT GAGGGGAATT   700
CACATAAATG GGATCAGGTC ATTCATTTAC GTTGTGTGCA AATATGATTT AAAGATACAA CCTTTGCAGA   770
GAGCATGCTT TCCTAAGGGT AGGCACGTGG AGGACTAAGG GTAAAGCATT CTTCAAGATC AGTTAATCAA   840

GAAAGGTGCT CTTTGCATTC TGAAATGCCC TTGTTGCAAA TATTGGTTAT ATTGATTAAA TTTACACTTA   910
ATGGAAACAA CCTTTAACTT ACAGATGAAC AAACCCACAA AAGCAAAAAA TCAAAAGCCC TACCTATGAT   980
TTCATATTTT CTGTGTAACT GGATTAAAGG ATTCCTGCTT GCTTTTGGGC ATAAATGATA ATGGAATATT  1050
TCCAGGTATT GTTTAAAATG AGGGCCCATC TACAAATTCT TAGCAATACT TTGGATAATT CTAAAATTCA  1120
GCTGGACATT GTCTAATTGT TTTTTATATA CATCTTTGCT AGAATTTCAA ATTTTAAGTA TGTGAATTTA  1190
GTTAATTAGC TGTGCTGATC AATTCAAAAA CATTACTTTC CTAAATTTTA GACTATGAAG GTCATAAATT  1260

CAACAAATAT ATCTACACAT ACAATTATAG ATTGTTTTTC ATTATAATGT CTTCATCTTA ACAGAATTGT  1330
CTTTGTGATT GTTTTTAGAA AACTGAGAGT TTTAATTCAT AATTACTTGA TCAAAAAATT GTGGGAACAA  1400
TCCAGCATTA ATTGTATGTG ATTGTTTTTA TGTACATAAG GAGTCTTAAG CTTGGTGCCT TGAAGTCTTT  1470
TGTACTTAGT CCCATGTTTA AAATTACTAC TTTATATCTA AAGCATTTAT GTTTTTCAAT TCAATTTACA  1540
TGATGCTAAT TATGGCAATT ATAACAAATA TTAAAGATTT CGAAATAGAA AAAAAAAAA AAA          1603
```

FIG. 8 cDNA sequence of PCGEM1 Seq. ID No .2

```
GCGGCCGCGT CGACGCAACT TCCTCTAATT GGGAAATAGT TAAGCAGATT CATAGAGCTG AATGATAAAA    70
TTGTACTTCG AGATGCACTG GGACTCAACG TGACCTTATC AAGTGAGATG GAGTCTTGCC CTGTCTCCAA   140
GGCTGGAGCC CAATGGTGTG ATCTTGGCTC ACTGCAACCT CCACCTCCCA GGTTCAAACG TTTCTCCTGC   210
CTCAGCCTCC CAAGTAACTG GGATTACAGC AGGCTTGGTG CATTTGACAC TTCATGATAT CAGCCAAAGT   280
GGAACTAAAA ACAGCTCCTG GAAGAGGACT ATGACATCAT CAGGTTGGGA GTCTCCAGGG ACAGCGGACC   350
CTTTGGAAAA GGACTAGAAA GTGTGAAATC TATTAGTCTT CGATATGAAA TTCTCTGTCT CCGTAAAAGC   420
ATTTCATATT TACAAGACAC AGGCCTACTC CTAGGGCAGC AAAAAGTGGC AACAGGCAAG CAGAGGGAAA   490
AGAGATCATG AGGCATTTCA GAGTGCACTG TCTTTTCATA TATTTCTCAA TGCCGTATGT TTGGTTTTAT   560
TTTGGCCAAG CATAACAATC TGCTCAAAAA AAAAAAATCT GGAGAAAACA AAGGTGCCTT TGCCAATGTT   630
ATGTTTCTTT TTGACAAGCC CTGAGATTTC TGAGGGGAAT TCACATAAAT GGGATCAGGT CATTCATTTA   700
CGTTGTGTGC AAATATGATT TAAAGATACA ACCTTTGCAG AGAGCATGCT TTCCTAAGGG TAGGCACGTG   770
GAGGACTAAG GGTAAAGCAT TCTTCAAGAT CAGTTAATCA AGAAAGGTGC TCTTTGCATT CTGAAATGCC   840
CTTGTTGCAA ATATTGGTTA TATTGATTAA ATTTACACTT AATGGAAACA ACCTTTAACT TACAGATGAA   910
CAAACCCCAC AAAAGCAAAA ATCAAAAGC CCTACCTATG ATTTCATATT TTCTGTGTAA CTGGATTAAA   980
GGATTCCTGC TTGCTTTTGG GCATAAATGA TAATGGAATA TTTCCAGGTA TTGTTTAAAA TGAGGGCCCA  1050
TCTACAAATT CTTAGCAATA CTTTGGATAA TTCTAAAATT CAGCTGGACA TTGTCTAATT GTTTTTTATA  1120
TACATCTTTG CTAGAATTTC AAATTTTAAG TATGTGAATT TAGTTAATTA GCTGTGCTGA TCAATTCAAA  1190
AACATTACTT TCCTAAATTT TAGACTATGA AGGTCATAAA TTCAACAAAT ATATCTACAC ATACAATTAT  1260
AGATTGTTTT TCATTATAAT GTCTTCATCT TAACAGAATT GTCTTTGTGA TTGTTTTTAG AAAACTGAGA  1330
GTTTTAATTC ATAATTACTT GATCAAAAAA TTGTGGGAAC AATCCAGCAT TAATTGTATG TGATTGTTTT  1400
TATGTACATA AGGAGTCTTA AGCTTGGTGC CTTGAAGTCT TTTGTACTTA GTCCCATGTT TAAAATTACT  1470
ACTTTATATC TAAAGCATTT ATGTTTTTCA ATTCAATTTA CATGATGCTA ATTATGGCAA TTATAACAAA  1540
TATTAAAGAT TTCGAAATAG AAAAAAAAAA AAAAATCTA                                    1579
```

FIG. 9 cDNA sequence of PCGEM1 Promoter Region Seq.ID No.3

```
TCCCTCTTGC GTTCTGCAAT TTCTGAAAAA AAGATGTTTA TTGCAAAGTG ATATGAGCAC TGGAAAGGTA   70
CTAATTCCAA TTTGATTCTA ATTGGATGAG TGACATGGGT AAGCGATTCT AAGCATTTGT GTTTTTTTA   140
GTAGTATGGA ATTTAATTAG TTCTCAGTAT GTTAGTGAAG ATGAATGAAA ACATGCATAT GTTTCCATGT  210
ATTATAAATA TTTTAAAATG CAAAAAATTA TTCTAATGAA TATATAAATA TAAAGCATAA CAATAATAAT  280
ACAATACCAC CCATAAAGTC ATCATCTAAT TTAAAAACTA AAACATTAAC ACTTGAATCT CCCCCATTGC  350
AACATCTTTC CCGACTTGTG TGTTTTTTTC TTTTGCTTTT AAAATTTTTG TTTTATCATA TGTCTGCATA  420
AGATTATATA GCTTTCCTTG TTTTAAGCTT TTTAAATAAT ATATTGTAGT TATATTATTT GTGCTTTGCT  490
TTTTTTACTT AACATTATGG TTCTAAAATT CAGTAATGTG TTGGGCATGT ATAATTTGTT TATTTTTAAT  560
CTCTTTGACA TTCGACTATA TAAATTTCAG TTTGTTTATT GACTCCTTTG TCTATAGATA CTCTGCTATT  630
TCTGTTTTTG CTGTTACAAA AATAATGCTG TTTTAAATTT CATTTTGTAT ACTTTTTTGA GGCATGTGTA  700
TGAGTTATTC TAAGGTAAAA AAATAAGAAA AAATTGCTGG GTTATAAGAT TGTCACATGC TCGAATTTAC  770
AAGATAATGC CAAATCATTT TTCAAAGTAA TTATACCTAT TTATACTACC GGTATGAGTA TATTGGTGCC  840
CACATAGTTG CTTGTTCTGC CAAAGTTTGG TATGATCGAA CAATAATTTT TGCCCATCAA ATGGCATAAA  910
ATAAAATCTC AGTGTGCTTT TAATTTGCAT TTTCTATGTT TAAGAATTGT TTCTTTTTTA ACCATTTATA  980
ATTTACTTTT GCTGAAATGC TTGCTTATTA TTTTTGCTCC CCATTTTTTC CTATTGGATT GCTTTTCTCA  1050
TTAATTTATA AGAATTTTAT ATGGTTTAGA TACTAATTAT TATATTACTG AAAATACCTT TATCAGTTTG  1120
TTGTGTACTT TCTACTTTAT GTCTTGTGAT GGATAAAAGT TTTAAATTGT ATTGTGTTGA AGTTAACATT  1190
TTTAAATTTT ATAATCAGCA TCTTTAATAA TCTCTTTMTA AAATTTTCCT TTACATAGAT GTCATAAAGA  1260
TACATCTCTA TAATTTCTTA TTTTTTTGGC ATATGTTCAT TAAGTCATTT TATCATTTTT TAGTAATAAA  1330
TTGCAGTTAT TTATGAAACA AATAATTTTT AAAATTATAT ATGCTTTCTT TAAAAATTGA TCTTAGCATG  1400
CTTCACTATG AAGCTTGAGG CTTCACTGCA CGTTGTACTG AAATTATGTA TAAAACAGTG GTTCTGAAAA  1470
TCTCTGAGTT CATGACACCT TTAGTGTCTC AGGTTTTTTT GCTTTTGTTC TTGTTTTTTC TCACAAAGCA  1540
CCTAAGTTAA ATAAAAACAA AGCACAAAGC TATCAGCTTC ATGTATTAAG TAGTAAGCTC CCATGTTAAC  1610
AGTTGTAACT TGCCTGGTGC CCAATAGATG TCACTCTGTT TTCCTAGAAA CTTTAAAATA TCCCTCAGTG  1680
CTCCTGTTAA TTCATGGTAG TGCCCCAAGG CACTCTGGCA CCCAGTTTTG GAACTGCAGT TTTAAAAGTC  1750
ATAAATTGAA TGAAAATGAT AGCAAAGGTG GAGGTTTTTA AAGAGCTATT TATAGGTCCC TGGACAGCA   1819
```

FIG. 11 cDNA sequence of PCGEM1 PROBE Seq.ID No.4

```
TTTTTTCAAT TAGGCAGCAA CCTTTTTGCC CTATGCCGTA ACCTGTGTCT GCAACTTCCT CTAATTGGGA    70
AATAGTTAAG CAGATTCATA GAGCTGAATG ATAAAATTGT ACTACGAGAT GCACTGGGAC TCAACGTGAC   140
CTTATCAAGT GAGCAGGCTT GGTGCATTTG ACACTTCATG ATATCATCCA AAGTGGAACT AAAAACAGCT   210
CCTGGAAGAG GACTATGACA TCATCAGGTT GGGAGTCTCC AGGGACAGCG GACCCTTTGG AAAAGGACTA   280
GAAAGTGTGA AATCTATTAG TCTTCGATAT GAAATTCTCT GTCTCTGTAA AAGCATTTCA TATTTACAAG   350
ACACAGGCCT ACTCCTAGGG CAGCAAAAAG TGGCAACAGG CAAGCAGAGG CAAAAGAGAT CATGAGGCAT   420
TTCAGAGTGC ACTGTCTTTT CATATATTTC TCAATGCCGT ATGTTTGGTT TTATTTTGGC CAAGCATAAC   490
AATCTGCTCA AGAAAAAAAA ATCTGGAGAA AACAAAGGTG CCTTTGCCAA TGTTATGTTT CTTTTTGACA   560
AGCCCTGAGA TTTCTGAGGG GAATTCACAT AAATGGGATC AGGTCATTCA TTTACGTTGT GTGCAAATAT   630
GATTTAAAGA TACAACCTTT GCAGAGAGCA TGCTTTCCTA AGGGTAGGCA CGTGGAGGAC TAAGGGTAAA   700
GCATTCTTCA AGATCAGTTA ATCAAGAAAG GTGCTCTTTG CATTCTGAAA TGCCCTTGTT GCAAATATTG   770
GTTATATTGA TTAAATTTAC ACTTAATGGA AACAACCTTT AACTTACAGA TGAACAAACC CACAAAAGCA   840
AAAAATCAAA AGCCCTACCT ATGATTTCAT ATTTTCTGTG TAACTGGATT AAAGGATTCC TGCTTGCTTT   910
TGGGCATAAA TGATAATGGA ATATTTCCAG GTATTGTTTA AAATGAGGGC CCATCTACAA ATTCTTAGCA   980
ATACTTTGGA TAATTCTAAA ATTCAGCTGG ACATTGTCTA ATTGT                             1025
```

FIG. 12

PCGEM1 Primers Used for PCR

PCR PRIMER 1 (SEQ ID No.5)

Sense Primer 5' TGCCTCAGCCTCCCAAGTAAC 3'

PCR PRIMER 2 (SEQ ID No.6)

Antisense Primers 5' GGCCAAAATAAAACCAAACAT 3'

PCR PRIMER 3 (SEQ ID No.7)

Sense Primer 5' TGGCAACAGGCAAGCAGAG 3'

FIG. 13

Complete Genomic DNA sequence of PCGEM1 gene.
TCCCTCTTGCGTTCTGCAATTTCTGAAAAAAAGATGTTTATTGCAAAGTGATATGAGCACTGGAAAGGTACTAATTCCAA
TTTGATTCTAATTGGATGAGTGACATGGGTAAGCGATTCTAAGCATTTGTGTTTTTTTTAGTAGTATGGAATTTAATTAG
TTCTCAGTATGTTAGTGAAGATGAATGAAAACATGCATATGTTTCCATGTATTATAAATATTTTAAAATGCAAAAAATTA
TTCTAATGAATATATAAATATAAAGCATAACAATAATAATACAATACCACCCATAAAGTCATCATCTAATTTAAAAACTA
AAACATTAACACTTGAATCTCCCCCATTGCAACATCTTTCCCGACTTGTGTGTTTTTTTCTTTTGCTTTTAAAATTTTTG
TTTTATCATATGTCTGCATAAGATTATATAGCTTTCCTTGTTTAAGCTTTTTAAATAATATATTGTAGTTATATTATTT
GTGCTTTGCTTTTTTTACTTAACATTATGGTTCTAAAATTCAGTAATGTGTTGGGCATGTATAATTTGTTTATTTTTAAT
CTCTTTGACATTCGACTATATAAATTTCAGTTTGTTTATTGACTCCTTTGTCTATACATACTCTGCTATTTCTGTTTTTG
CTGTTACAAAAATAATGCTGTTTTAAATTTCATTTTGTATACTTTTTTGAGGCATGTGTATGAGTTATTCTAAGGTAAAA
AAATAAGAAAAAATTGCTGGGTTATAAGATTGTCACATGCTCGAATTTACAAGATAATGCCAAATCATTTTTCAAAGTAA
TTATACCTATTTATACTACCGGTATGAGTATATTGGTGCCCACATAGTTGCTTGTTCTGCCAAAGTTTGGTATGATCGAA
CAATAATTTTTGCCCATCAAATGGCATAAAATAAAATCTCAGTGTGCTTTTAATTTGCATTTTCTATGTTTAAGAATTGT
TTCTTTTTTAACCATTTATAATTTACTTTTGCTGAAATGCTTGCTTATTATTTTTGCTCCCCATTTTTTCCTATTGGATT
GCTTTTCTCATTAATTTATAAGAATTTTATATGGTTTAGATACTAATTATTATATTACTGAAAATACCTTTATCAGTTTG
TTGTGTACTTTCTACTTTATGTCTTGTGATGGATAAAAGTTTTAAATTGTATTGTCTTGAAGTTAACATTTTTAAATTTT
ATAATCAGCATCTTTAATAATCTCTTTATAAAATTTTCCTTTACATAGATGTCATAAAGATACATCTCTATAATTTCTTA
TTTTTTTGGCATATGTTCATTAAGTCATTTTATCATTTTTTAGTAATAAATTGCAGTTATTTATGAAACAAATAATTTTT
AAAATTATATATGCTTTCTTTAAAAATTGATCTTAGCATGCTTCACTATGAAGCTTGAGGCTTCACTGCACGTTGTACTG
TTGTTTTTTGTCACAAAGCACCTAAGTTAAATAAAAACAAAGCACAAAGCTATCAGCTTCATGTATTAAGTAGTAAGCTC
CCATGTTAACAGTTGTAACTTGCCTGGTGCCCAATAGATGTCACTCTGTTTTCCTAGAAACTTTAAAATATCCCTCAGTG
CTCCTGTTAATTCATGGTAGTGCCCCAAGGCACTCTGGCACCCAGTTTTGGAACTGCAGTTTTAAAAGTCATAAATTGAA
TGAAAATGATAGCAAAGGTGGAGGTTTTTAAAGAGCTATTTATACCTCCCTGGACAGCATCTTTTTTCAATTAGGCAGCA
ACCTTTTTGCCTATGCCGTAACTGTGTCTGCACTTCCTCTAATTGGGGTGAGTAAGAGATTTTGTTATGTATATAATAGC
TAAGAATATAGTAATAATCCCTTAAATCATGGTTATTTTTAAACTACTAACATTTAGAAGACAAAATAAAAATGCTTTGA
AAAGTATAGAGGTTTTAGTGTAATTAGCAGGGAATAATGAAATGATTTGATAGGGCTACTCAGTTTTGTATAACTTTGGT
GCTTTAAGTCTGAATGCAGAGCATGGATGTTGTGATCCAGCCTTTATATGTTTTCCCTGAAGAAGATTTAATTTATTTGG
CCTTTTGAGAAACACATTTGGCATTGTAATATGTTTTGCTTCCAGGTTCTATCTCCAAGGATAATTTGACAAAATCACAC
ATAAATTTATTTTCAGGGCACACAGTTTCCCTTTTAGGGAACTCACAGAGGTAGAGAGTAATACAATAATCACATTTGAA
TATTCAGTAAGTGAGGTCCTCATAGATCTTATGTGTATGTCACCATGTATATAATTTTGTTAATCACTAGATGTATGAGA
CAAGAAATTTGAGGAATCTTAACTAGAGATTAAAATCAGGGATTTAAATCAAAGAAACATTTAAATGCCTCCTTTATTAT
TTAAATACCTGCATGGGAGAATCATTGAAAAAAAAATAAAAAGCATACAACTTGGGAATATTATAAACCAAGAAGAATTT
GTTATTCTGGTTGATTTTTTTTCAGGCTCCGCACAGGCAACTTACCTTTATCTCTTTGTGATTTTTATTTCTTGTTAAA
ATATACAGAAATAGTTAAGCAGATTCATAGAGCTGAATATAAAATTTACTACGAGATGCACTGGGACTCAACGTGACCTT
ATCAAGTGACTTATCAGTGAGGTGAGCATTCTTAATTCAGATAATGGAACTTATTATCATAATCTTTTGCTTATGCTATT
GTTGAGCTTAACTACTTATTCATATTTGCATATGCATATTGAGATAATATCATTTCATTAATTTCAGTACTGAACACTAA
TCTCCTAAGAGTAATTGTGAAAGTTTCAGATTGCACTATTTTAACTATATATCTGTATGTTATCTTCATATATGCTTGA
ATAACTTATAAGCAATTGAAACTTTCAATTACAGTATACTATTGAAGCAAATCAACAAATATATACACATATCCATTAGC
AATAGTAGATAATTTTTGTAAATGTCCAGCACAGTTCTTCATATGTAGAGGATGTTCAAATTGGCTAAGTTCCTTTTCTC
TCTTAATTATTAGTATTTTTCCTACTGCTCTTTGTATAATTATTCCTTCCTCTTTAGCTCCAATCCTTACAATCTATTCT

*FIG. 14*

```
TAACATAGCAACTGGGAAGAAAGTTTTTAAACATAAACCAGATGATGTCACTCCACCCCACAAAACTTCCACTATTCTCT
GTCACACATAGAAAGAAAGAAAAAAAAATATTGAAAACCTACAAAGACTTGCTATGATCTGGTCCAGGCTCTCCCTAAAAT
TTCATGTAATTTCCAGCCACTAGGCCTTTCTGGCTCTCCTTCAATCTCATTAGCCTTTTCACTACTACAAGTTAGACTGG
GTTTTGGCCGAGGTATTTCTTTTTTTCATATTTTGCCTTTGCCTAGATTGCTCTTCCAATAGATATTCACAATTGCATCA
TCATTTCTATATACGTGCTAAAAGGTTTCCTTGTCCAAAATAGCTTCAGTGACCACCTGATCTAGAATAGTCTCGATCAA
AAGTTTCTTTTCCTTTTCCTCACCACTTGATATTTATATCAAACATTTATTTGTGTAATTTATGTGTTTGTTTGTTTTCT
GTACTAGCATTATGATGACCATACTATTTGATGCCCCCCAAAAAATACTTTCGAGAATGACAGGGCAAAGCTAAAATAAT
TAAATTATATAATTTTGACATAGGCACTATTGACAAAAAGCAATTGATGTTATGATAGTGTTAGATCTATGAAATAGTAC
TATTTAAAAGTAATTCTCTGAAATACAATTTTCTAAAACTAAAAGCAGCATATGTACATGAAACACCAAAAAACTTCCTT
ATATTTATCACTGGAAGATTTAAAATAGTATAAGTAGTAACTTATTTAATATATTTTTGATTATTTAATTAATTTTATAG
TATCCAACTCTAATATAATGCCACTGGTATTTGTTCAAAATATTTTAATGTTGTCTATTTATTTTTAATTTGCCTAAAAA
TTATCTTAAATGAAAATTTTTGGTTAATAAATTTGAAAATACTGAAACCCTCATCTCCAGTCTCTGTGGATCCTAAAGTT
TTTAGTTGAGAAAATAATTTTTCTCTAGAGAATGAAGTAGCTTGTAAGCTTGGAGAAATTTCTGCTAAATAAATGATATT
ATCAACTCTTATTTCTTCAATACGAAATATATAAATATTTCAGCTCATATATTTTTGCAGGTGCTATGCTTTTGCTTCC
AATCATAATTTCTGACAAATATTTTGGAAGTCAAAACTTGTCTTCTATTTTGTTATTTAAAATTATATAGACTACTTTTG
TAAACCTTTATACTATCAAATCATAGGCAATTTCAGTTTGATTTCATTCTGGTGCAGAATATAAGTTTATCCAAGTAAAA
CAGGAGTCACTTCAAAAGATTCCTCCCACTGACTGAGATATTCCAAAGCCAACTTTGCAAAATTTCAGAATTAAATATTA
TACTTCTTTGTACCTTCATTTTATTTGTTCAATTTTCTTTGTGTTTGTAGAAAATTTTAATATTTTCTGTTTTCAAGT
TTTGATTTTAATTTACTACTTTATAATTTTTAAAGGTAAGTTTTGTGAGGCTATATTCATTATGTGTTTTGAATAAAGAC
ATACAATTAATTTTGAGAACTGCAATAAAAATTATAAGACTATTAAAAATGCAGTAAGTGTACTACACTTAGGCTGCTAA
AAATGCAGTACCAGTAGACTACATTTAGGCTGCTTAAAGTTAGTTCTTCTAAGTACCATATACTTTAAAATTTTAGCTAA
TGATGGAGAACAAAGACAGAAAGACTGTGTTACCATATTCTAGTTGGCCATTTTGTTTTGTTTTGAGAGACGTCACATCA
GCCTTATCATAAAAATTATTTGGTTTTACCATTTTGACTGTGAGCAAAATATACAGCATAATATACAAAATAAAATACAT
GTACATCTTCACAACTTCTTGTTTAGGATGCAATTATATATATATATATATATATATTTATTATTATACTTTAAGTTCTA
GGGTACATGGCACCACGTGCAGGTTGTTACATATGTATACATGTGCCATGTTGGTGTGCTGCACCCATTAACTCGTCATT
TACATTAGGTGTATCTCCTAATGCTATCCCTCCCCTCTCTCCCCACCCCACAACAAGCCCCGGTGTGTGATGTTCCCCTT
CCTGTGTCCATGTGTTCTCATTGTTCAATTCCCACCTATGAGTGAGAACACGCAGTGTTTGCTTTTTTGTCCTTGCAATA
GTTTGCTGAGAATGATGGTTTCCAGCTTCATCCATGTCCCTACAAAGGACATGAACTCATCATTTTTTATGGCTGCATAG
TATTCCATGGTGTATATGTGCCACCATTTTCTTAATCCGAGTCTGTCCATTGTTGTTGGACATTTGGGTTGCAATTTTGA
GTTTCATGTGTAGCATGTATAGCACAACCAATTAAGATTTCTTTCTTTCTCTCTTTTTTTTTTTTTTTGTTGAAATGGA
GTCTTGCCTGTCTCCAAGGCTGGAGCCCAATGGTGTGATCTTGGCTTACTGCAACCTCCACCTCCCGGGTTCAAGCGATT
CTCCTGCCTCAGCCATCCGAGTAGCTGGGACTATAGGCGTGCACCACCATGCCCAGCTAATTTTTGTATTTTTAGTACAG
ACGGGGTTTCACCACGGTGGCCAGGATGGTCTCAATTTCTTGACCTCATGATTCACCCGCCTTGGCCTCCCAAAGTGCTG
GGATTACAGGTGTGAACCACCAAGCCCGGCCTGTCACAAGTTTTTAGTGTTCTATTTTAATACAGAAATTAGATAAATCC
AAAGAGAAAGACATTTCATATGTGCGTAGAGTTGTCGGAAGAAATGAGAGTCTTATAAATAACTTTAAAAATTGTGAAGA
AATAAAGGCAAAATAGTCCTATGCAGTTTGATTTAAATATATTCTTAATAAGAGCTACTTTTGTGAAACCAGAATAATTG
AAACATGTAGATATGGATCTTCATTAGTGACTGACATAATATATTGTTATTGTTACTATTTTATTGTATCAGCCAACTAA
TATTGAGTGCTTTGTGTATCCTAAGCACTATGCTAAACACTGTACCAGTATTACCTGATATAATCATATTAATATTTATT
```

FIG. 14(cont'd-1)

```
ATTTCACTTTTCATATGAAAAAATTGAAGCACAGATTAAGACACTCCGAAATCATACCTCTATTGATTATCAGCACCAGG
ATTTGAATTGAGGCACTCTGATCCAGAGAAGCTTTTGTTTCCATGAAGGCTTATGTTGGGGAAAAATAATCAAATTGCCT
GTACCTCAGTTGTATAAATAAGAGGTTGGGTTGGTAGATGATTCTGGCTGATTCAGCAGAAAAGAAATTTATTCAAAGGA
TATCACACAGTTTTCATAACAGTTAAGAATACAGAGGAAACAGGGCACCAGGGCTAAGTACAGACCAAAGTCCAAAACCA
CTGCCAAAGTTGCAGCAAGGAGAACAGCACAAATTTGCTTGCTGTCACCCGCCACTAGATGCTTTTGTTTGGAGCCTTGA
ACTTGACTTACACTGCCACTGACATCAGCACCAGTGCTCTCTGTGTACTAGGAGGTGGAGTTGGTGACGTTGCTGAACTA
AAAGCAGATGTTTCTGCTGTGAAATAGATACCTAATACAGAACCTGATTCCTCATTCATTCCCTCCCCAAATCATATGCT
TGTAGTGTGGCTAGAGTTTCTGTTTCTCCTTGGTCCAGGCAGAATTTATGAAGCTTGCTATTTATCGCCTTAAAGATTAG
AAGAATATTCATAAGGTATTAGATTGCCATAAGGTTGAACAAATCAACATTCAACTTCAAGGATTCAACATTGTTTTGTT
TTCTTTTGGGATACCTCTGCAGCAGTTCAAATCTTATTTCTGCCCTTGGACAACCAGGTTTATAAATATTGCAGATTCTC
CACTGACTGCTTTGATCCTATCTTCTATATTTATGTATACTAATTAGCATATAATAAAAGATTATGTTACAGAATCTCAA
AATTAGTAATTATGAATTGAGATGGTGTTATACAGTACACTAACATCCAAGAGACTTGTTTATTCCAAGGAAAATATTTA
GAGATATTAAATGATATTTCTCATCCTTTAGACATATACATTTTTTAGCTTACAGCCTGCTTTAGGCAAGCAACAGACTC
TCAGGATCTGCTCCTACCAGGGTCTGAACATTTCCTCCCAGTTTTAAAGAAACAAATTCAAATAACATTGTAACCTCCAG
AGGAAAGTTCAAGGTCTTTTATAGTATTGTTTAAACAGTACAGCTGAGGAAACTAAAGACAGAGAAGTTAAATGCCTTGG
CACTTAGTCTAGATTTACAATAAACTCCTYTCTACTTAGGACCCACTAACAGGGGCTGCATTTACACCAAAACCATGAAG
GTGGCCCAAGTCATCACTGAGAAGTAGTACAAGCACCGAGGGAATGACTTCAACAGGAACAAGAAAGCGTGGAAGGAGAT
CCTAGCAGGAAGCTCCACAAGAAGATAGCATGTTACGTCTTGCATTGGATGAAGCAGGTTCAGAGAGACCTAGTGACAGC
TATCTCCGTCAAGGTGCAGAAGGAGAGATCATTGAATGTAGCATTTTCATGCAAAAAAAAAAATGTTGAAGTCTTTGGAC
TTCGGGAGTCTGTCCAAACTGCAGGTCACTCAGCCTACAGTTGGGATGAATTTCAAAACACCAGTTGGAGCCGGTTGAAT
CTTTCTGCTATGCTGTAATATTTTCAGTAAACCCAGCGCAACAACAACAACAAAACACAAAAGGAGGAGAAGCAGCCAAG
TCTCTTGGTTTACAGAGTAGCTCCTAATACCCCTTGCTGTCTGTCTCAAGTGCCCAATGGGAAGATAGTCAAAACAATAT
TCACACCTGTGATTCATCTCTCTACATGCAGTGTGTGTGAATCTTTATATACTGCATATTAAGGATCTGTCTTTACAGAT
AAAAACTAAAGCATTGAAGGAACTCCTTGTTTTGACTTATCAAAGTCCTTAAGAAAATACTAGAAAATTATAGCCATTGT
TTCAAATTTTAGCTTTATATTATCACTTGAAATGTGATGAAATGTGGCTGATAGATAATAATTCACTGATAACCTACAGA
CAATTCCCATCTTAAAATGGACCATTGGATTGAAGAATTAAATAAAATTGAGGGTTTTCCTTACATGTTTTGTCTAAAGA
GCGAAGTAGAAACAACTGTTCATAGATCTTCATTGAGGATTCGCATGTGAAGTAAGTACTCCTAACATAAACAAGTGGAC
TTATCAACCAAGTTCCATAAATCATGAACAAAAATATTTGTCCCCAGAGAGACTATTTTTCCACCACATCTCTTGTAATA
AACACAGAGCCCAGTTCAGTTAAAATACTTTAAGGGTGGACGGTTCAGGGCCTGCTGAGTGGCACTCAGTAAGAAAACCC
AGCAGAACATTTACTTCTCTCTTTATTCCAGAGCATCAATGGCCAAGGCTGGAAGATCCCAGAACACTGAACAGACATTT
GGTCTCTTATGGCCTGCCAATTTTCACAGTGGGTTCCAACGCTTTGGGTCAAACCAAAATAGACCTGTTAGAAAAATGTC
GGTTGGAATACGCTAACAATAAGACAGAATAAATGTGATTATTTCACCTCATTTTTATAGGACTTGAGTAATTTTATTAT
AACATTCTTGAGGGCTGGAAAATCTGAATGTTAGGACACCAAATATCTCCAGAAAACAAGTTTTATATTTCTAATCCTGC
ATAATAAACCTGGGGCCACTGCAGGCCTCATTAATAAAAACCTAATGGTATAACAATAATGAGGAGGAAATGCCAATGCC
GCACAAATCTGTTGAGACTAAAATATTTCTCACCCCAGCAGGCTTGGTGCATTTGACACTTCATGATATCAGCCAAAGTG
GAACTAAAAACAGCTCCTGGAAGAGGACTATGACATCATCAGGTTGGGAGTCTCCAGGGACAGCGGACCCTTTGGAAAAG
GACTAGAAAGTGTGAAATCTATTAGTCTTCGATATGAAATTCTCTGTCTCTGTCAAAAGCATTTCATATTTACAAGACAC
AGGCCTACTCCTAGGGCAGCAAAAAGTGGCAACAGGCAAGCAGAGGGAAAAGAGATCATGAGGCATTTCAGAGTGCACTG
```

FIG. 14(cont'd-2)

```
TCTTTTCATATATTTCTCAATGCCGTATGTTTGGTTTTATTTTGGCCAAGCATAACAATCTGCTCAAGAAAAAAAAATCT
GGAGAAAACAAAGGTGCCTTTGCCAATGTTATGTTTCTTTTTGACAAGCCCTGAGATTTCTGAGGGGAATTCACATAAAT
GGGATCAGGTCATTCATTTACGTTGTGTGCAAATATGATTTAAAGATACAACCTTTGCAGAGAGCATGCTTTCCTAAGGG
TAGGCACGTGGAGGACTAAGGGTAAAGCATTCTTCAAGAATCAGTTAATCAAAGAAAGGTGCTCTTTGCATTCTGAAATG
CCCTTGTTGCAAATATTGGTTATATTGATTAAATTTACACTTAATGGAAACAACCTTTAACTTACAGATGAACAAACCCA
CAAAAGCAAAAAAGCAAAAGCCCGACCTATGATTTCATATTTTCTGTGTAACTGGATTAAAGGATTCCTGCTTGCTTTTG
GGCATAAATGATAATGGAATATTTCCAGGTATTGTTTAAAATGAGGGCCCATCTACAAATTCTTAGCAATACTTTGGATA
ATTCTAAAATTCAGCTGGACATTGTCTAATTGTTTTTTATATACATCTTTGCTAGAATTTCAAATTTTAAGTATGTGAAT
TTAGTTAATTAGCTGTGCTGATCAATTCAAAAACATTACTTTCCTAAATTTTAGACTATGAAGGTCATAAATTCAACAAA
TATATCTACACATACAATTATAGATTGTTTTTCATTATAATGTCTTCATCTTAACAGAATTGTCTTTGTGATTGTTTTTA
GAAAACTGAGAGTTTTAATTCATAATTACGTTGATCAAAAAATTGTGGGAACAATCCAGCATTAATTGTATGTGATTGTT
TTTATGTACATAAGGAGTCTTAAGCTTGGTGCCTTGAAGTCTTTTGTACTTAGTCCCATGTTTAAAATTACTACTTTATA
TCTAAAGCATTTATGTTTTTCAATTCAATTTACATGATGCTAATTATGGCAATTATAACAAATATTAAAGATTTCGAAAT
AGAATATGTGAATTGTTCACCATACATAGAAATGAAAAGTTCATTTCGTAAAGCAAGATGCTGGGTGAAAGAGTGCTTTT
GATTGAAAGATCACTAGATTAGTAGAGGGCAAGACTTTTAGTCCCTAATCTACCCTTAATAGCCATGTGGTCACGTGTAA
GTCAGTGAACCCATCTCATTCTCCTCATACTTTTTTCATCTCTAAAATGAGGGTATAATTTAAGCTCGTTCATTTTTTTT
TTTTTTTGAGATAGAGTTTTGCTCTTGTCACCCAGGTTGGAGTGCAATGGCACGATCTCAGCTCACTGCAACCCTCTGCT
TCCTCGGTTCAAGTGATTCTCCCTGCTTCAGCCTCCCAAGTGAGCCCGGGATTACAGGTGCCCGCCACCACATCTGGGCC
TAGATTTTTTGTATTTTCACCATGTTGGCCAGGCTGGTCTCGAACCCCTACCTCAGGTGATCCCTCGCCTCGGCCTCTCA
AAGTGCTGGGATTACAGGTGTGAGCCACCACGCCCAGCCCAATATCAGTTTTTCTTTTTTAACACAAGGCTAACACAATC
AAAATACTAGCTAGGGGAGAAAAAAAAAATAAGGCACTGTTTATGTGTAACAGGCTCTTGTTGCAATCCACTGGGGCAGA
CCAAATAAACAGTAAGAATCAAATCCTTTTCATATAATCCTTTCTTTGCAGAATACATAAAATCCCCACAAATGGCTTAT
CTTCCTTTTTATGATATGTTGGAGAATTGTAGCTAAGTGACAGATATTTTGCTTGGGTGTATAGACCACAAAGGACTGTG
TCTTGATGATGGTTTGCATAAAATTATACCTTAGTTTTTACTTTGTATGTTACATGTTAGATTTAGAGTATGAAAATTAG
TAGGGAGGATTATTAACAAAGAACAGGGCAAGAGGAGTAGAATTAAACCTCTTCTAATACCTGTGCACAAGTAGGCTTTT
CAGAAACTCTACAACCCCAACATAAACTGGATAGTTAGAAAAGCACACTCCCAAGGAAGGCGGTTATGTTTTGCAGTTTG
AATCAGAAGAATAGAGCTATAGCAATCTTCATTCTATAGTAACATTAAAGAGCCTGGTTTATATTATAGCAGTCATTAAG
ATTTAAAAATTTACATCTTGCCGTTCTTCTTACTCACAGATTTTCGAGAGGTAATGTAATGATCACACGAGGTGAGAATC
ACTGCCTTTTATAATGCGATTAAATGCATGAACAAAGTTTCCAACAAATAACAGTAATAAAAAGAAACATGTATTAGCAC
TTAATAAGCCAGGTGCTGTACGACGTGTGTTACATGCTTTCAATCCATGAACTGGTAAACTGGTACTAGTATCTCTATTG
GACATGTGAGGAAACCAAATGGAGTTGATAAACAGTAGAGTTAAAAATTACTCTTCATATATTATATTGCCTCAATCTCA
CAGACATCTCTGCTACCAAAAGCTATCATATCTAGACTCGA
```

FIG. 14(cont'd-3)

PROSTATE-SPECIFIC GENE, PCGEM1, AND THE METHODS OF USING PCGEM1 TO DETECT, TREAT, AND PREVENT PROSTATE CANCER

CROSS REFERENCE TO RELATED APPLICATIONS

The present application is based upon U.S. provisional application Ser. No. 60/126,469, filed Mar. 26, 1999, priority to which is claimed under 35 U.S.C. §119(e). The entire disclosure of U.S. provisional application Ser. No. 60/126,469 is expressly incorporated herein by reference.

GOVERNMENT INTEREST

The invention described herein may be manufactured, licensed, and used for governmental purposes without payment of royalties to us thereon.

FIELD OF THE INVENTION

The present invention relates to nucleic acids that are expressed in prostate tissue. More particularly, the present invention relates to the first of a family of novel, androgen-regulated, prostate-specific genes, PCGEM1, that is overexpressed in prostate cancer, and methods of using the PCGEM1 sequence and fragments thereof to measure the hormone responsiveness of prostate cancer cells and to detect, diagnose, prevent and treat prostate cancer and other prostate related diseases.

BACKGROUND

Prostate cancer is the most common solid tumor in American men (1). The wide spectrum of biologic behavior (2) exhibited by prostatic neoplasms poses a difficult problem in predicting the clinical course for the individual patient (3, 4). Public awareness of prostate specific antigen (PSA) screening efforts has led to an increased diagnosis of prostate cancer. The increased diagnosis and greater number of patients presenting with prostate cancer has resulted in wider use of radical prostatectomy for localized disease (5). Accompanying the rise in surgical intervention is the frustrating realization of the inability to predict organ-confined disease and clinical outcome for a given patient (5, 6). Traditional prognostic markers, such as grade, clinical stage, and pretreatment PSA have limited prognostic value for individual men. There is clearly a need to recognize and develop molecular and genetic biomarkers to improve prognostication and the management of patients with clinically localized prostate cancer. As with other common human neoplasia (7), the search for molecular and genetic biomarkers to better define the genesis and progression of prostate cancer is the key focus for cancer research investigations worldwide.

The new wave of research addressing molecular genetic alterations in prostate cancer is primarily due to increased awareness of this disease and the development of newer molecular technologies. The search for the precursor of prostatic adenocarcinoma has focused largely on the spectrum of microscopic changes referred to as "prostatic intraepithelial neoplasia" (PIN). Bostwick defines this spectrum as a histopathologic continuum that culminates in high grade PIN and early invasive cancer (8). The morphologic and molecular changes include the progressive disruption of the basal cell-layer, changes in the expression of differentiation markers of the prostatic secretory epithelial cells, nuclear and nucleolar abnormalities, increased cell proliferation, DNA content alterations, and chromosomal and allelic losses (8, 9). These molecular and genetic biomarkers, particularly their progressive gain or loss, can be followed to trace the etiology of prostate carcinogenesis. Foremost among these biomarkers would be the molecular and genetic markers associated with histological phenotypes in transition between normal prostatic epithelium and cancer. Most studies so far seem to agree that PIN and prostatic adenocarcinoma cells have a lot in common with each other. The invasive carcinoma more often reflects a magnification of some of the events already manifest in PIN.

Early detection of prostate cancer is possible today because of the widely propagated and recommended blood PSA test that provides a warning signal for prostate cancer if high levels of serum PSA are detected. However, when used alone, PSA is not sufficiently sensitive or specific to be considered an ideal tool for the early detection or staging of prostate cancer (10). Combining PSA levels with clinical staging and Gleason scores is more predictive of the pathological stage of localized prostate cancer (11). In addition, new molecular techniques are being used for improved molecular staging of prostate cancer (12, 13). For instance, reverse transcriptase—polymerase chain reaction (RT-PCR) can measure PSA of circulating prostate cells in blood and bone marrow of prostate cancer patients.

Despite new molecular techniques, however, as many as 25 percent of men with prostate cancer will have normal PSA levels—usually defined as those equal to or below 4 nanograms per milliliter of blood (14). In addition, more than 50 percent of the men with higher PSA levels are actually cancer free (14). Thus, PSA is not an ideal screening tool for prostate cancer. More reliable tumor-specific biomarkers are needed that can distinguish between normal and hyperplastic epithelium, and the preneoplastic and neoplastic stages of prostate cancer.

Identification and characterization of genetic alterations defining prostate cancer onset and progression is important in understanding the biology and clinical course of the disease. The currently available TNM staging system assigns the original primary tumor (T) to one of four stages (14). The first stage, T1, indicates that the tumor is microscopic and cannot be felt on rectal examination. T2 refers to tumors that are palpable but fully contained within the prostate gland. A T3 designation indicates the cancer has spread beyond the prostate into surrounding connective tissue or has invaded the neighboring seminal vesicles. T4 cancer has spread even further. The TNM staging system also assesses whether the cancer has metastasized to the pelvic lymph nodes (N) or beyond (M). Metastatic tumors result when cancer cells break away from the original tumor, circulate through the blood or lymph, and proliferate at distant sites in the body.

Recent studies of metastatic prostate cancer have shown a significant heterogeneity of allelic losses of different chromosome regions between multiple cancer foci (21–23). These studies have also documented that the metastatic lesion can arise from cancer foci other than dominant tumors (22). Therefore, it is critical to understand the molecular changes which define the prostate cancer metastasis especially when prostate cancer is increasingly detected in early stages (15–21).

Moreover, the multifocal nature of prostate cancer needs to be considered (22–23) when analyzing biomarkers that may have potential to predict tumor progression or metastasis. Approximately 50–60% of patients treated with radical prostatectomy for localized prostate carcinomas are found to have microscopic disease that is not organ confined, and a significant portion of these patients relapse (24). Utilizing biostatistical modeling of traditional and genetic biomarkers such as p53 and bcl-2, Bauer et al. (25–26) were able to identify patients at risk of cancer recurrence after surgery. Thus, there is clearly a need to develop biomarkers defining various stages of the prostate cancer progression.

Another significant aspect of prostate cancer is the key role that androgens play in the development of both the normal prostate and prostate cancer. Androgen ablation, also referred to as "hormonal therapy," is a common treatment for prostate cancer, particularly in patients with metastatic disease (14). Hormonal therapy aims to inhibit the body from making androgens or to block the activity of androgen. One way to block androgen activity involves blocking the androgen receptor; however, that blockage is often only successful initially. For example, 70–80% of patients with advanced disease exhibit an initial subjective response to hormonal therapy, but most tumors progress to an androgen-independent state within two years (16). One mechanism proposed for the progression to an androgen-independent state involves constitutive activation of the androgen signaling pathway, which could arise from structural changes in the androgen receptor protein (16).

As indicated above, the genesis and progression of cancer cells involve multiple genetic alterations as well as a complex interaction of several gene products. Thus, various strategies are required to fully understand the molecular genetic alterations in a specific type of cancer. In the past, most molecular biology studies had focused on mutations of cellular proto-oncogenes and tumor suppressor genes (TSGs) associated with prostate cancer (7). Recently, however, there has been an increasing shift toward the analysis of "expression genetics" in human cancer (27–31), i.e., the under-expression or over-expression of cancer-specific genes. This shift addresses limitations of the previous approaches including: 1) labor intensive technology involved in identifying mutated genes that are associated with human cancer; 2) the limitations of experimental models with a bias toward identification of only certain classes of genes, e.g., identification of mutant ras genes by transfection of human tumor DNAs utilizing NIH3T3 cells; and 3) the recognition that the human cancer associated genes identified so far do not account for the diversity of cancer phenotypes.

A number of studies are now addressing the alterations of prostate cancer-associated gene expression in patient specimens (32–36). It is inevitable that more reports on these lines are to follow.

Thus, despite the growing body of knowledge regarding prostate cancer, there is still a need in the art to uncover the identity and function of the genes involved in prostate cancer pathogenesis. There is also a need for reagents and assays to accurately detect cancerous cells, to define various stages of prostate cancer progression, to identify and characterize genetic alterations defining prostate cancer onset and progression, to detect micro-metastasis of prostate cancer, and to treat and prevent prostate cancer.

SUMMARY OF THE INVENTION

The present invention relates to the identification and characterization of a novel gene, the first of a family of genes, designated PCGEM1, for Prostate Cancer Gene Expression Marker 1. PCGEM1 is specific to prostate tissue, is androgen-regulated, and appears to be over-expressed in prostate cancer. More recent studies associate PCGEM1 cDNA with promoting cell growth. The invention provides the isolated nucleotide sequence of PCGEM1 or fragments thereof and nucleic acid sequences that hybridize to PCGEM1. These sequences have utility, for example, as markers of prostate cancer and other prostate related diseases, and as targets for therapeutic intervention in prostate cancer and other prostate related diseases. The invention further provides a vector that directs the expression of PCGEM1, and a host cell transfected or transduced with this vector.

In another embodiment, the invention provides a method of detecting prostate cancer cells in a biological sample, for example, by using nucleic acid amplification techniques with primers and probes selected to bind specifically to the PCGEM1 sequence. The invention further comprises a method of selectively killing a prostate cancer cell, a method of identifying an androgen responsive cell line, and a method of measuring responsiveness of a cell line to hormone-ablation therapy.

In another aspect, the invention relates to an isolated polypeptide encoded by the PCGEM1 gene or a fragment thereof, and antibodies generated against the PCGEM1 polypeptide, peptides, or portions thereof, which can be used to detect, treat, and prevent prostate cancer.

Additional features and advantages of the invention will be set forth in the description which follows, and in part will be apparent from the description, or may be learned by practice of the invention. The objectives and other advantages of the invention will be realized and attained by the sequences, cells, vectors, and methods particularly pointed out in the written description and claims herein as well as the appended drawings.

BRIEF DESCRIPTION OF THE DRAWINGS

FIG. 2 depicts a differential display pattern of MRNA obtained from matched tumor and normal tissues of a prostate cancer patient. Arrows indicate differentially expressed cDNAs.

FIG. 3 depicts the analysis of PCGEM1 expression in primary prostate cancers.

FIG. 6b depicts a RNA master blot showing the prostate tissue specificity of PCGEM1.

FIG. 8 depicts a cDNA sequence of PCGEM1 (SEQ ID NO:1).

FIG. 9 depicts an additional cDNA sequence of PCGEM1 (SEQ ID NO:2).

FIG. 11 depicts the cDNA sequence of the promoter region of PCGEM1 SEQ ID NO:3.

FIG. 12 depicts the cDNA of a probe, designated SEQ ID NO:4.

FIG. 13 depicts the cDNAs of primers 1–3, designated SEQ ID NOs:5–7, respectively.

FIG. 14 depicts the genomic DNA sequence of PCGEM1, designated SEQ ID NO:8.

DETAILED DESCRIPTION OF THE INVENTION

Figure 1:
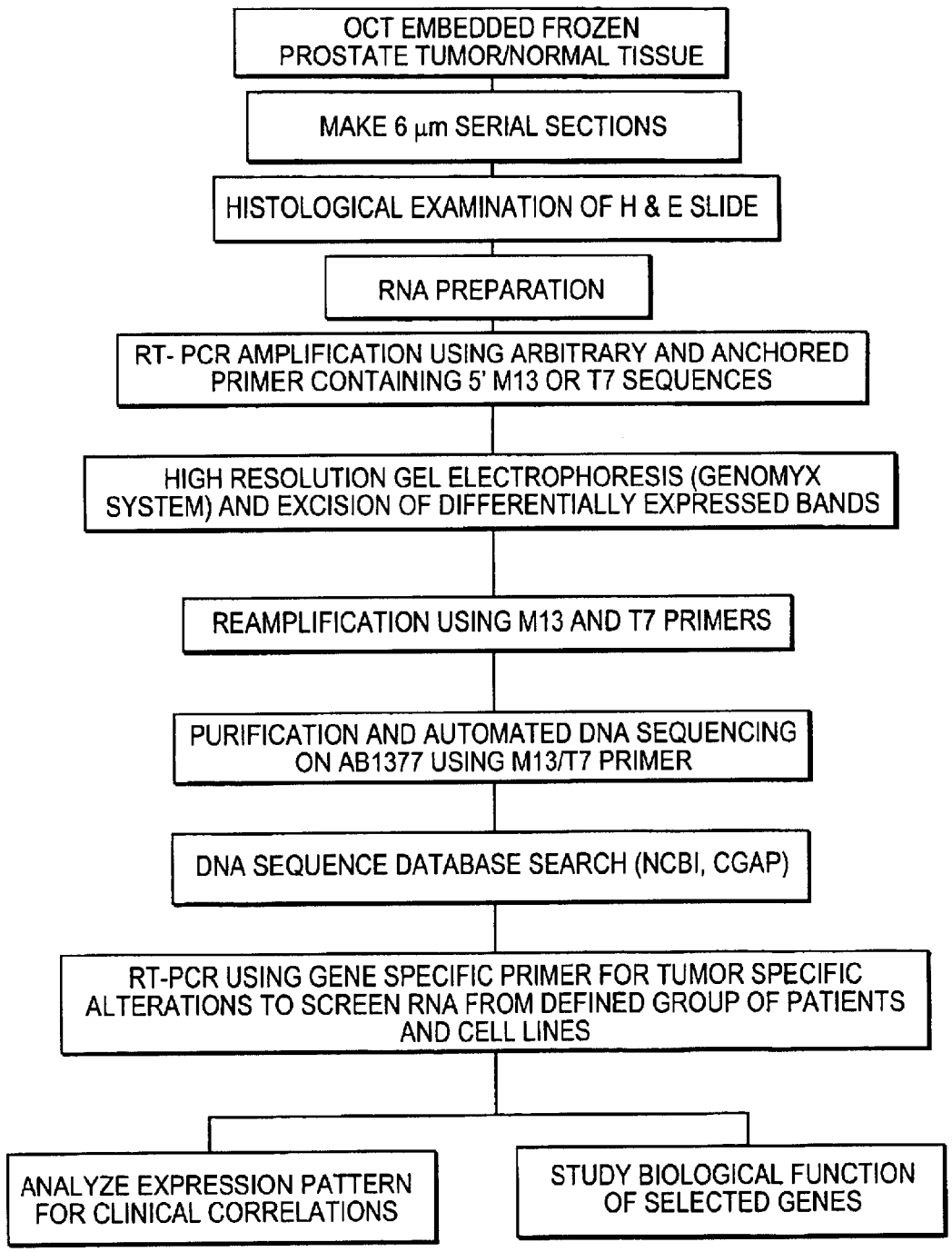
FIG. 1 depicts the scheme for the identification of differentially expressed genes in prostate tumor and normal tissues.
Figure 4:
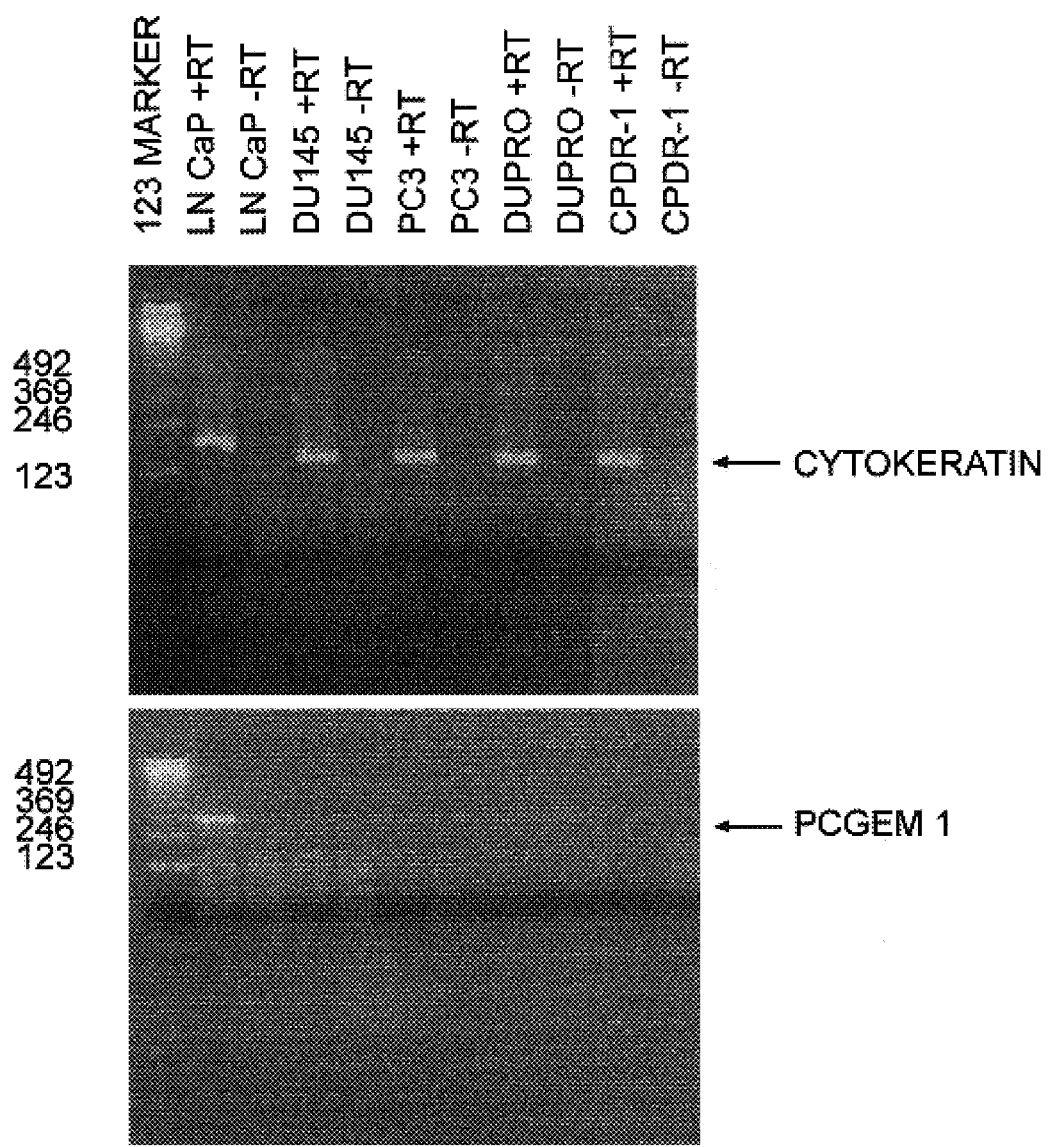
FIG. 4 depicts the expression pattern of PCGEM1 in prostate cancer cell lines.

The present invention relates to PCGEM1, the first of a family of genes, and its related nucleic acids, proteins, antigens, and antibodies for use in the detection, prevention, and treatment of prostate cancer (e.g., prostatic intraepithelial neoplasia (PIN), adenocarcinomas, nodular hyperplasia, and large duct carcinomas) and prostate related diseases (e.g., benign prostatic hyperplasia), and kits comprising these reagents.

Although we do not wish to be limited by any theory or hypothesis, preliminary data suggest that the PCGEM1 nucleotide sequence may be related to a family of non-coding poly A+RNA that may be implicated in processes relating to growth and embryonic development (40–44). Evidence presented herein supports this hypothesis. Alternatively, PCGEM1 cDNA may encode a small peptide.

Nucleic Acid Molecules

In a particular embodiment, the invention relates to certain isolated nucleotide sequences that are substantially free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual,* 2nd ed., Cold Spring Harbor Laboratory, Cold Spring Harbor, N.Y. (1989)).

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO:1, SEQ ID NO:2, or suitable fragments thereof, as a probe.

The DNA molecules of the invention include full length genes as well as polynucleotides and fragments thereof. The full length gene may include the N-terminal signal peptide. Although a non-coding role of PCGEM1 appears likely, the possibility of a protein product cannot presently be ruled out. Therefore, other embodiments may include DNA encoding a soluble form, e.g., encoding the extracellular domain of the protein, either with or without the signal peptide.

The nucleic acids of the invention are preferentially derived from human sources, but the invention includes those derived from non-human species, as well.

Preferred Sequences

Particularly preferred nucleotide sequences of the invention are SEQ ID NO:1, SEQ ID NO:2, and SEQ ID NO: 8, as set forth in FIGS. 8, 9, and 14, respectively. Two cDNA clones having the nucleotide sequences of SEQ ID NO:1 and SEQ ID NO:2, and the genomic DNA having the nucleotide sequence of SEQ ID NO: 8, were isolated as described in Example 2.

Thus, in a particular embodiment, this invention provides an isolated nucleic acid molecule selected from the group consisting of (a) the polynucleotide sequence of SEQ ID NO:1, SEQ ID NO:2, or SEQ ID NO: 8; (b) an isolated nucleic acid molecule that hybridizes to either strand of a denatured, double-stranded DNA comprising the nucleic acid sequence of (a) under conditions of moderate stringency in 50% formamide and about 6×SSC at about 42° C. with washing conditions of approximately 60° C., about 0.5×SSC, and about 0.1% SDS; (c) an isolated nucleic acid molecule that hybridizes to either strand of a denatured, double-stranded DNA comprising the nucleic acid sequence of (a) under conditions of high stringency in 50% formamide and about 6×SSC, with washing conditions of approximately 68° C., about 0.2×SSC, and about 0.1% SDS; (d) an isolated nucleic acid molecule derived by in vitro mutagenesis from SEQ ID NO:1, SEQ ID NO:2, or SEQ ID NO:8; (e) an isolated nucleic acid molecule degenerate from SEQ ID NO:1, SEQ ID NO:2, or SEQ ID NO:8 as a result of the genetic code; and (f) an isolated nucleic acid molecule selected from the group consisting of human PCGEM1 DNA, an allelic variant of human PCGEM1 DNA, and a species homolog of PCGEM1 DNA.

As used herein, conditions of moderate stringency can be readily determined by those having ordinary skill in the art based on, for example, the length of the DNA. The basic conditions are set forth by Sambrook et al. *Molecular Cloning: A Laboratory Manual,* 2d ed. Vol. 1, pp. 1.101–104, Cold Spring Harbor Laboratory Press, (1989), and include use of a prewashing solution for the nitrocellulose filters of about 5×SSC, about 0.5% SDS, and about 1.0 mM EDTA (pH 8.0), hybridization conditions of about 50% formamide, about 6×SSC at about 42° C. (or other similar hybridization solution, such as Stark's solution, in about 50% formamide at about 42° C.), and washing conditions of about 60° C., about 0.5×SSC, and about 0.1% SDS. Conditions of high stringency can also be readily determined by the skilled artisan based on, for example, the length of the DNA. Generally, such conditions are defined as hybridization conditions as above, and with washing at approximately 68° C., about 0.2×SSC, and about 0.1% SDS. The skilled artisan will recognize that the temperature and wash solution salt concentration can be adjusted as necessary according to factors such as the length of the probe.

Additional Sequences

Due to the known degeneracy of the genetic code, wherein more than one codon can encode the same amino acid, a DNA sequence can vary from that shown in SEQ ID NO:1, SEQ ID NO:2, or SEQ ID NO:8, and still encode PCGEM1. Such variant DNA sequences can result from silent mutations (e.g., occurring during PCR amplification), or can be the product of deliberate mutagenesis of a native sequence.

The invention thus provides isolated DNA sequences of the invention selected from: (a) DNA comprising the nucleotide sequence of SEQ ID NO:1, SEQ ID NO:2, or SEQ ID NO:8; (b) DNA capable of hybridization to a DNA of (a) under conditions of moderate stringency; (c) DNA capable of hybridization to a DNA of (a) under conditions of high stringency; and (d) DNA which is degenerate as a result of the genetic code to a DNA defined in (a), (b), or (c). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region. Of course, should PCGEM1 encode a polypeptide, polypeptides encoded by such DNA sequences are encompassed by the invention. Conditions of moderate and high stringency are described above.

In another embodiment, the nucleic acid molecules of the invention comprise nucleotide sequences that are at least 80% identical to a nucleotide sequence set forth herein. Also contemplated are embodiments in which a nucleic acid molecule comprises a sequence that is at least 90% identical, at least 95% identical, at least 98% identical, at least 99% identical, or at least 99.9% identical to a nucleotide sequence set forth herein.

Percent identity may be determined by visual inspection and mathematical calculation. Alternatively, percent identity of two nucleic acid sequences may be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353–358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence of this invention or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); *Recombinant DNA Methodology,* Wu et al., eds., Academic Press, Inc., San Diego (1989), pp. 189–196; and *PCR Protocols: A Guide to Methods and Applications,* Innis et al., eds., Academic Press, Inc. (1990).

Use of PCGEM1 Nucleic Acid or Oligonucleotides

In a particular embodiment, the invention relates to PCGEM1 nucleotide sequences isolated from human prostate cells, including the complete genomic DNA (FIG. 14, SEQ ID NO: 8), and two full length cDNAs: SEQ ID NO:1 (FIG. 8) and SEQ ID NO:2 (FIG. 9), and fragments thereof. The nucleic acids of the invention, including DNA, RNA, mRNA and oligonucleotides thereof, are useful in a variety of applications in the detection, diagnosis, prognosis, and treatment of prostate cancer. Examples of applications within the scope of the present invention include, but are not limited to:

amplifying PCGEM1 sequences;

detecting a PCGEM1-derived marker of prostate cancer by hybridization with an oligonucleotide probe;

identifying chromosome 2;

mapping genes to chromosome 2;

identifying genes associated with certain diseases, syndromes, or other conditions associated with human chromosome 2;

constructing vectors having PCGEM1 sequences;

expressing vector-associated PCGEM1 sequences as RNA and protein;

detecting defective genes in an individual;

developing gene therapy;

developing immunologic reagents corresponding to PCGEM1-encoded products; and treating prostate cancer using antibodies, antisense nucleic acids, or other inhibitors specific for PCGEM1 sequences.

Detecting, Diagnosing, and Treating Prostate Cancer

The present invention provides a method of detecting prostate cancer in a patient, which comprises (a) detecting PCGEM1 mRNA in a biological sample from the patient; and (b) correlating the amount of PCGEM1 mRNA in the sample with the presence of prostate cancer in the patient. Detecting PCGEM1 mRNA in a biological sample may include: (a) isolating RNA from said biological sample; (b) amplifying a PCGEM1 cDNA molecule; (c) incubating the PCGEM1 cDNA with the isolated nucleic acid of the invention; and (d) detecting hybridization between the PCGEM1 cDNA and the isolated nucleic acid. The biological sample can be selected from the group consisting of blood, urine, and tissue, for example, from a biopsy. In a preferred embodiment, the biological sample is blood. This method is useful in both the initial diagnosis of prostate cancer, and the later prognosis of disease. This method allows for testing prostate tissue in a biopsy, and after removal of a cancerous prostate, continued monitoring of the blood for micrometastases.

According to this method of diagnosing and prognosticating prostate cancer in a patient, the amount of PCGEM1 mRNA in a biological sample from a patient is correlated with the presence of prostate cancer in the patient. Those of ordinary skill in the art can readily assess the level of over-expression that is correlated with the presence of prostate cancer.

In another embodiment, this invention provides a vector, comprising a PCGEM1 promoter sequence operatively linked to a nucleotide sequence encoding a cytotoxic protein. The invention further provides a method of selectively killing a prostate cancer cell, which comprises introducing the vector to prostate cancer cells under conditions sufficient to permit selective killing of the prostate cells. As used herein, the phrase "selective killing" is meant to include the killing of at least a cell which is specifically targeted by a nucleotide sequence. The putative PCGEM1 promoter, contained in the 5' flanking region of the PCGEM1 genomic sequence, SEQ ID NO: 3, is set forth in FIG. 11. Applicants envision that a nucleotide sequence encoding any cytotoxic protein can be incorporated into this vector for delivery to prostate tissue. For example, the cytotoxic protein can be ricin, abrin, diphtheria toxin, p53, thymidine kinase, tumor necrosis factor, cholera toxin, *Pseudomonas aeruginosa* exotoxin A, ribosomal inactivating proteins, or mycotoxins such as trichothecenes, and derivatives and fragments (e.g., single chains) thereof.

This invention also provides a method of identifying an androgen-responsive cell line, which comprises (a) obtaining a cell line suspected of being androgen-responsive, (b) incubating the cell line with an androgen; and (c) detecting PCGEM1 mRNA in the cell line, wherein an increase in PCGEM1 mRNA, as compared to an untreated cell line, correlates with the cell line being androgen-responsive.

The invention further provides a method of measuring the responsiveness of a prostatic tissue to hormone-ablation therapy, which comprises (a) treating the prostatic tissue with hormone-ablation therapy; and (b) measuring PCGEM1 mRNA in the prostatic tissue following hormone-ablation therapy, wherein a decrease in PCGEM1 mRNA, as compared to an untreated cell line, correlates with the cell line responding to hormone-ablation therapy.

In another aspect of the invention, these nucleic acid molecules may be introduced into a recombinant vector, such as a plasmid, cosmid, or virus, which can be used to transfect or transduce a host cell. The nucleic acids of the present invention may be combined with other DNA sequences, such as promoters, polyadenylation signals, restriction enzyme sites, multiple cloning sites, and other coding sequences.

Probes

Among the uses of nucleic acids of the invention is the use of fragments as probes or primers. Such fragments generally comprise at least about 17 contiguous nucleotides of a DNA sequence. The fragment may have fewer than 17 nucleotides, such as, for example, 10 or 15 nucleotides. In other embodiments, a DNA fragment comprises at least 20, at least 30, or at least 60 contiguous nucleotides of a DNA sequence. Examples of probes or primers of the invention include those of SEQ ID NO: 5, SEQ ID NO: 6, and SEQ ID NO: 7, as well as those disclosed in Table I.

However, even larger probes may be used. For example, a particularly preferred probe is derived from PCGEM1 (SEQ ID NO: 1) and comprises nucleotides 116 to 1140 of that sequence. It has been designated SEQ ID NO: 4 and is set forth in FIG. 12.

When a hybridization probe binds to a target sequence, it forms a duplex molecule that is both stable and selective. These nucleic acid molecules may be readily prepared, for example, by chemical synthesis or by recombinant techniques. A wide variety of methods are known in the art for detecting hybridization, including fluorescent, radioactive, or enzymatic means, or other ligands such as avidin/biotin.

In another aspect of the invention, these nucleic acid molecules may be introduced into a recombinant vector, such as a plasmid, cosmid, or virus, which can be used to transfect or transduce a host cell. The nucleic acids of the present invention may be combined with other DNA sequences, such as promoters, polyadenylation signals, restriction enzyme sites, multiple cloning sites, and other coding sequences.

Because homologs of SEQ ID NO: 1, SEQ ID NO: 2, and SEQ ID NO: 8 from other mammalian species are contemplated herein, probes based on the human DNA sequence of SEQ ID NO: 1, SEQ ID NO: 2, and SEQ ID NO: 8 may be used to screen cDNA libraries derived from other mammalian species, using conventional cross-species hybridization techniques.

In another aspect of the invention, one can use the knowledge of the genetic code in combination with the sequences set forth herein to prepare sets of degenerate oligonucleotides. Such oligonucleotides are useful as primers, e.g., in polymerase chain reactions (PCR), whereby DNA fragments are isolated and amplified. Particularly preferred primers are set forth in FIG. 13 and Table I and are designated SEQ ID NOS: 5–7 and 9–22, respectively. A particularly preferred primer pair is p518 (SEQ ID NO: 15) and p839 (SEQ ID NO: 22), which when used in PCR, preferentially amplifies mRNA, thereby avoiding less desirable cross-reactivity with genomic DNA.

Chromosome Mapping

As set forth in Example 3, the PCGEM1 gene has been mapped by fluorescent in situ hybridization to the 2q32 region of chromosome 2 using a bacterial artificial chromosome (BAC) clone containing PCGEU1 genomic sequence. Thus, all or a portion of the nucleic acid molecule of SEQ ID NO:1, SEQ ID NO:2, and SEQ ID NO:8, including oligonucleotides, can be used by those skilled in the art

TABLE I

| Primer | Sequence (5' → 3') | S/AS | Starting Base # | SEQ ID NO. |
|---|---|---|---|---|
| p413 | TGGCAACAGGCAAGCAGAG | S | 496 | SEQ ID NO: 9 |
| p414 | GGCCAAAATAAAACCAAACAT | AS | 596 | SEQ ID NO: 10 |
| p489 | GCAAATATGATTTAAAGATACAAC | S | 738 | SEQ ID NO: 11 |
| p490 | GGTTGTATCTTTAAATCATATTTGC | AS | 762 | SEQ ID NO: 12 |
| p491 | ACTGTCTTTTCATATATTTCTCAATC | S | 546 | SEQ ID NO: 13 |
| p517 | AAGTAGTAATTTTAAACATGGGAC | AS | 1502 | SEQ ID NO: 14 |
| p518 | TTTTTCAATTAGGCAGCAACC | S | 117 | SEQ ID NO: 15 |
| p519 | GAATTGTCTTTGTGATTGTTTTTAG | S | 1324 | SEQ ID NO: 16 |
| p560 | CAATTCACAAAGACAATTCAGTTAG | AS | 1341 | SEQ ID NO: 17 |
| p561 | ACAATTAGACAATGTCCAGCTGA | AS | 1140 | SEQ ID NO: 18 |
| p562 | CTTTGGCTGATATCATGAAGTGTC | AS | 308 | SEQ ID NO: 19 |
| p623 | AACCTTTTGCCCTATGCCGTAAC | S | 134 | SEQ ID NO: 20 |
| p624 | GAGACTCCCAACCTGATGATGT | AS | 364 | SEQ ID NO: 21 |
| p839 | GGTCACGTTGAGTCCCAGTG | AS | 256 | SEQ ID NO: 22 | using well-known techniques to identify human chromosome 2, and the specific locus thereof, that contains the PCGEM1 DNA. Useful techniques include, but are not limited to, using the nucleotide sequence of SEQ ID NO:1, SEQ ID NO:2, or SE ID NO:8, or fragments thereof, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybridization. First, PCR is performed using the Whitehead Institute/MIT Center for Genome Research Genebridge4 panel of 93 radiation hybrids (http://www-genome.wi.mit.edu/ftp/distribution/human_STS_releases/july97/rhmap/genebridge4.html). Primers are used which lie within a putative exon of the gene of interest and which amplify a product from human genomic DNA, but do not amplify hamster genomic DNA. The results of the PCRs are converted into a data vector that is submitted to the Whitehead/MIT Radiation Mapping site on the internet (http://www-seq.wi.mit.edu). The data is scored and the chromosomal assignment and placement relative to known Sequence Tag Site (STS) markers on the radiation hybrid map is provided. (The following web site provides additional information about radiation hybrid mapping: http://www-genome.wi.mit.edu/ftp/distribution/human_STS_releases/july97/07-97.INTRO.html).

Identifying Associated Diseases

As noted above, PCGEM1 has been mapped to the 2q32 region of chromosome 2. This region is associated with specific diseases, which include but are not limited to diabetes mellitus (insulin dependent), and T cell leukemia/lymphoma. Thus, the nucleic acids of SEQ ID NO: 1, SEQ ID NO: 2, or SEQ ID NO:8, or fragments thereof, can be used by one skilled in the art using well-known techniques to analyze abnormalities associated with gene mapping to chromosome 2. This enables one to distinguish conditions in which this marker is rearranged or deleted. In addition, nucleotides of SEQ ID NO:1, SEQ ID NO:2, or SEQ ID NO:8, or fragments thereof, can be used as a positional marker to map other genes of unknown location.

The DNA may be used in developing treatments for any disorder mediated (directly or indirectly) by defective, or insufficient amounts of PCGEM1, including prostate cancer. Disclosure herein of native nucleotide sequences permits the detection of defective genes, and the replacement thereof with normal genes. Defective genes may be detected in in vitro diagnostic assays, and by comparison of a native nucleotide sequence disclosed herein with that of a gene derived from a person suspected of harboring a defect in this gene.

Sense-Antisense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA (SEQ ID NO:1, SEQ ID NO:2, or SEQ ID NO:8). Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

The biologic activity of PCGEM1 in assay cells and the over expression of PCGEM1 in prostate cancer tissues suggest that elevated levels of PCGEM1 promote prostate cancer cell growth. Thus, the antisense oligonucleotides to PCGEM1 may be used to reduce the expression of PCGEM1 and, consequently, inhibit the growth of the cancer cells.

Binding of antisense or sense oligonucleotides to target nucleic acid sequences results in the formation of duplexes. The antisense oligonucleotides thus may be used to block expression of proteins or to inhibit the function of RNA. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides. Such modifications may modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, $CaPO_4$-mediated DNA transfection, electroporation, or by using gene transfer vectors such as Epstein-Barr virus or adenovirus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Polypeptides and Fragments Thereof

The invention also encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

The polypeptides of the invention include full length proteins encoded by the nucleic acid sequences set forth above. The polypeptide's of the invention may be membrane bound or they may be secreted and thus soluble. The invention also includes the expression, isolation and purification of the polypeptides and fragments of the invention, accomplished by any suitable technique.

The following examples further illustrate preferred aspects of the invention.

EXAMPLE 1
Differential Gene Expression Analysis in Prostate Cancer

Using the differential display technique, we identified a novel gene that is over-expressed in prostate cancer cells. Differential display provides a method to separate and clone individual messenger RNAs by means of the polymerase chain reaction, as described in Liang et al., *Science*, 257:967–71 (1992), which is hereby incorporated by reference. Briefly, the method entails using two groups of oligonucleotide primers. One group is designed to recognize the polyadenylate tail of messenger RNAs. The other group contains primers that are short and arbitrary in sequence and anneal to positions in the messenger RNA randomly distributed from the polyadenylate tail. Products amplified with these primers can be differentiated on a sequencing gel based on their size. If different cell populations are amplified with the same groups of primers, one can compare the amplification products to identify differentially expressed RNA sequences.

Differential display ("DD") kits from Genomyx (Foster City, Calif.) were used to analyze differential gene expression. The steps of the differential display technique are summarized in FIG. 1. Histologically well defined matched tumor and normal prostate tissue sections containing approximately similar proportions of epithelial cells were chosen from individual prostate cancer patients.

Genomic DNA-free total RNA was extracted from this enriched pool of cells using RNAzol B (Tel-Test, Inc., Friendswood, Tex.) according to manufacturer's protocol. The epithelial nature of the RNA source was further confirmed using cytokeratin 18 expression (45) in reverse transcriptase-polymerase chain reaction (RT-PCR) assays. Using arbitrary and anchored primers containing 5' M13 or T7 sequences (obtained from Biomedical Instrumentation Center, Uniformed Services University of the Health Sciences, Bethesda), the isolated DNA-free total RNA was amplified by RT-PCR which was performed using ten anchored antisense primers and four arbitrary sense primers according to the protocol provided by Hieroglyph™ RNA Profile Kit 1 (Genomyx Corporation, CA). The cDNA fragments produced by the RT-PCR assay were analyzed by high resolution gel electrophoresis, carried out by using Genomyx™ LR DNA sequencer and LR-Optimized™ HR-1000™ gel formulations (Genomyx Corporation, CA).

A partial DD screening of normal/tumor tissues revealed 30 differentially expressed cDNA fragments, with 53% showing reduced or no expression in tumor RNA specimens and 47% showing over expression in tumor RNA specimen (FIG. 2). These cDNAs were excised from the DD gels, reamplified using T7 and M13 primers and the RT PCR conditions recommended in Hieroglyph™ RNA Profile Kit-1 (Genomyx Corp., CA), and sequenced. The inclusion of T7 and M13 sequencing primers in the DD primers allowed rapid sequencing and orientation of cDNAs (FIG. 1).

All the reamplified cDNA fragments were purified by Centricon-c-100 system (Amicon, USA). The purified fragments were sequenced by cycle sequencing and DNA sequence determination using an ABI 377 DNA sequencer. Isolated sequences were analyzed for sequence homology with known sequences by running searches through publicly available DNA sequence databases, including the National Center for Biotechnology Information and the Cancer Genome Anatomy Project. Approximately two-thirds of these cDNA sequences exhibited homology to previously described DNA sequences/genes e.g., ribosomal proteins, mitochondrial DNA sequences, growth factor receptors, and genes involved in maintaining the redox state in cells. About one-third of the cDNAs represented novel sequences, which did not exhibit similarity to the sequences available in publicly available databases. The PCGEM1 fragment, obtained from the initial differential display screening represents a 530 base pair (nucleotides 410 to 940 of SEQ ID NO: 1) cDNA sequence which, in initial searches, did not exhibit any significant homology with sequences in the publicly available databases. Later searching of the high throughput genome sequence (HTGS) database revealed perfect homology to a chromosome 2 derived uncharacterized, unfinished genomic sequence (accession # AC 013401).

EXAMPLE 2
Characterization of Full Length PCGEM1 cDNA Sequence

The full length of PCGEM1 was obtained by 5' and 3' RACE/PCR from the original 530 bp DD product (nucleotides 410 to 940 of PCGEM1 cDNA SEQ ID NO:1) using a normal prostate cDNA library in lambda phage (Clontech, CA). The RACE/PCR products were directly sequenced. Lasergene and MacVector DNA analysis software were used to analyze DNA sequences and to define open reading frame regions. We also used the original DD product to screen a normal prostate cDNA library. Three overlapping cDNA clones were identified.

Sequencing of the cDNA clones was performed on an ABI-310 sequence analyzer and a new dRhodamine cycle sequencing kit (PE-Applied Biosystem, CA). The longest PCGEM1 cDNA clone, SEQ ID NO:1 (FIG. 8), revealed 1603 nucleotides with a potential polyadenylation site, ATTAAA, close to the 3' end followed by a poly (A) tail. As noted above, although initial searching of PCGEM1 gene in publically available DNA databases (e.g., National Center for Biotechnology Information) using the BLAST program did not reveal any homology, a recent search of the HTGS database revealed perfect homology of PCGEM1 (using cDNA of SEQ ID NO:1) to a chromsome 2 derived uncharacterized, unfinished genomic sequence (accession #AC 013401). One of the cDNA clones, SEQ ID NO:2 (FIG. 9), contained a 123 bp insertion at 278, and this inserted sequence showed strong homology (87%) to Alu sequence. It is likely that this clone represented the premature transcripts. Sequencing of several clones from RT-PCR further confirmed the presence of the two forms of transcripts.

Sequence analysis did not reveal any significant long open reading frame in both strands. The longest ORF in the sense strand was 105 nucleotides (572–679) encoding 35 amino acid peptides. However, the ATG was not in a strong context of initiation. Although we could not rule out the coding capacity for a very small peptide, it is possible that PCGEM1 may function as a non-coding RNA.

Figure 15:
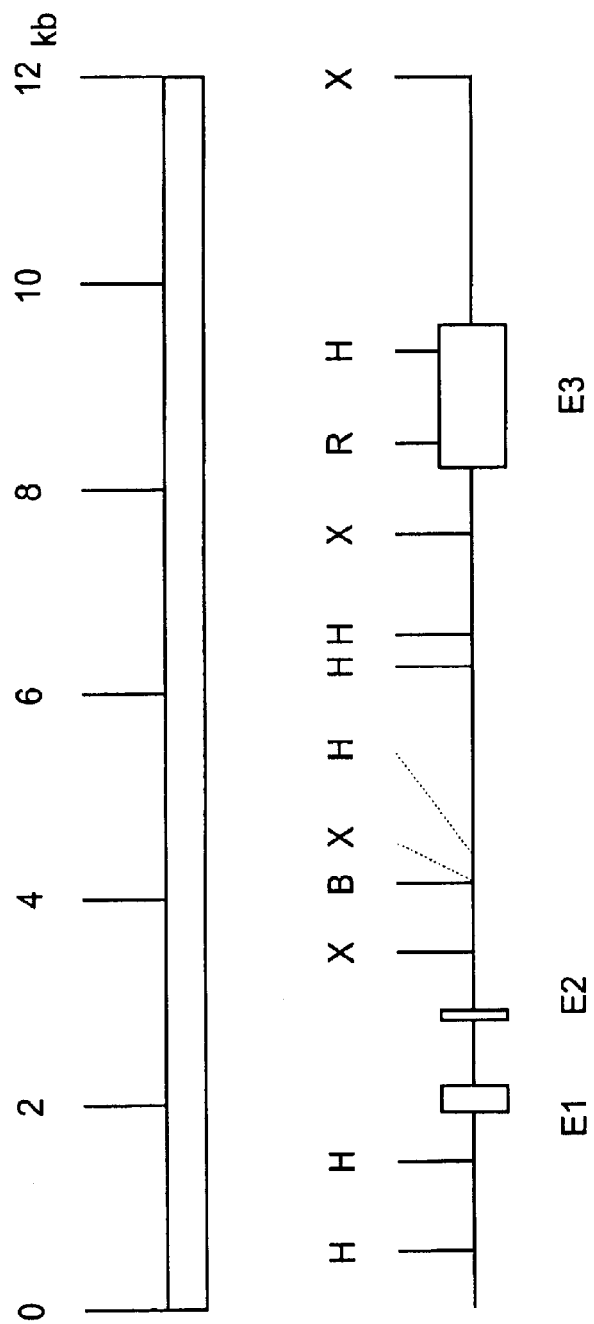
FIG. 15 depicts the structure of the PCGEM1 transcription unit.

The sequence of PCGEM1 cDNA has been verified by several approaches including characterization of several clones of PCGEM1 and analysis of PCGEM1 cDNAs amplified from normal prostate tissue and prostate cancer cell lines. We have also obtained the genomic clones of PCGEM1, which has helped to confirm the PCGEM1 cDNA sequence. The complete genomic DNA sequence of PCGEM1 (SEQ ID NO:8) is shown in FIG. 14. In FIG. 14 (and in the accompanying Sequence Listing), "Y" represents any one of the four nucleotide bases, cylosine, thymine, adenine, or guanine. Comparison of the cDNA and genomic sequences revealed the organization of the PCGEM1 transcription unit from three exons (FIG. 15: E, Exon; B: BamHI; H: HindIII; X: XbaI; R: EcoRI).

EXAMPLE 3
Mapping the Location of PCGEM1

Figure 7A:
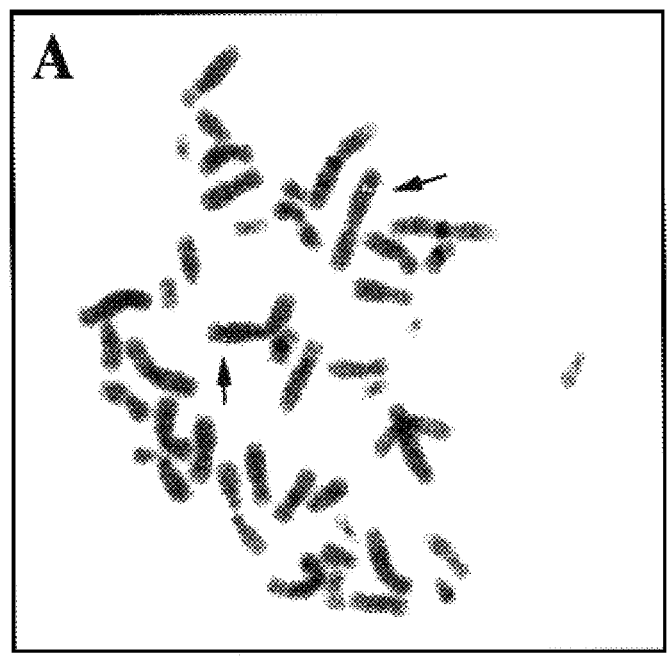
FIG. 7A depicts the chromosomal localization of PCGEM1 by fluorescent in situ hybridization analysis.
Figure 7B:
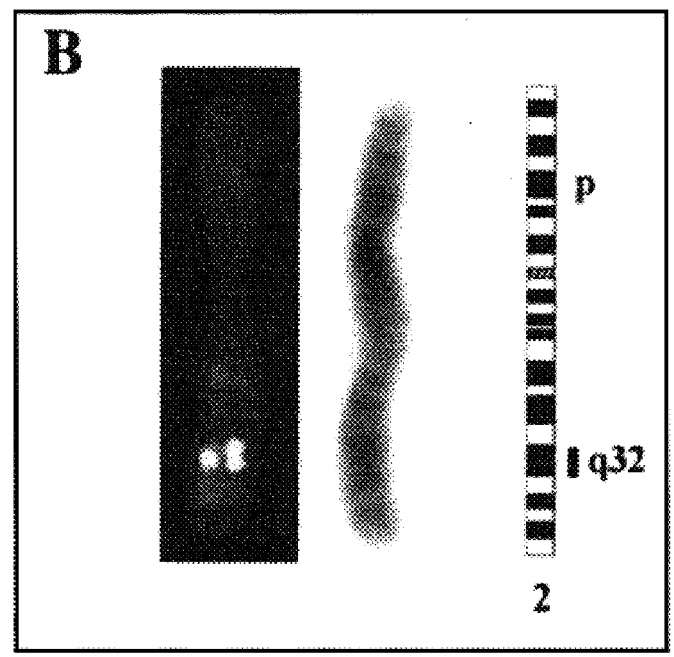
FIG. 7B depicts a DAPI counter-stained chromosome 2 (left), an inverted DAPI stained chromosome 2 shown as G-bands (center), and an ideogram of chromosome 2 showing the localization of the signal to band 2q32(bar).

Using fluorescent in situ hybridization and the PCGEM1 genomic DNA as a probe, we mapped the location of PCGEM1 on chromosome 2q to specific region 2q32 (FIG. 7A). Specifically, a Bacterial Artificial Chromosome (BAC) clone containing the PCGEM1 genomic sequence was isolated by custom services of Genome Systems (St. Louis, Mo.). PCGEM1-Bac clone 1 DNA was nick translated using spectrum orange (Vysis) as a direct label and flourescent in situ hybridization was done using this probe on normal human male metaphase chromosome spreads. Counterstaining was done and chromosomal localization was determined based on the G-band analysis of inverted 4',6-diamidino-2-phenylindole (DAPI) images. (FIG. 7B: a DAPI counterstained chromosome 2 is shown on the left; an inverted DAPI stained chromosome 2 shown as G-bands is shown in the center; an ideogram of chromosome 2 showing the localization of the signal to band 2q32(bar) is shown on the right.) NU200 image acquisition and registration software was used to create the digital images. More than 20 metaphases were analyzed.

EXAMPLE 4
Analysis of PCGEM1 Gene Expression in Prostate Cancer

To further characterize the tumor specific expression of the PCGEM1 fragment, and also to rule out individual variations of gene expression alterations commonly observed in tumors, the expression of the PCGEM1 fragment was evaluated on a test panel of matched tumor and normal RNAs derived from the microdissected tissues of twenty prostate cancer patients.

Using the PCGEM1 cDNA sequence (SEQ ID NO:1), specific PCR primers (Sense primer 1 (SEQ ID NO: 5): 5' TGCCTCAGCCTCCCAAGTAAC 3' and Antisense primer 2 (SEQ ID NO: 6): 5' GGCCAAAATAAAACCAAACAT 3') were designed for RT-PCR assays. Radical prostatectomy derived OCT compound (Miles Inc. Elkhart, Ind.) embedded fresh frozen normal and tumor tissues from prostate cancer patients were characterized for histopathology by examining hematoxylin and eosin stained sections (46). Tumor and normal prostate tissues regions representing approximately equal number of epithelial cells were dissected out of frozen sections. DNA-free RNA was prepared from these tissues and used in RT-PCR analysis to detect PCGEM1 expression. One hundred nanograms of total RNA was reverse transcribed into cDNA using RT-PCR kit (Perkin-Elmer, Foster, Calif.). The PCR was performed using Amplitaq Gold from Perkin-Elmer (Foster, Calif.). PCR cycles used were: 95° C. for 10 minutes, 1 cycle; 95° C. for 30 seconds, 55° C. for 30 seconds, 72° C. for 30 seconds, 42 cycles, and 72° C. for 5 minutes, 1 cycle followed by a 4° C. storage. Epithelial cell-associated cytokeratin 18 was used as an internal control.

RT-PCR analysis of microdissected matched normal and tumor tissue derived RNAs from 23 CaP patients revealed tumor associated overexpression of PCGEM1 in 13 (56%) of the patients (FIG. 5). Six of twenty-three (26%) patients did not exhibit detectable PCGEM1 expression in either normal or tumor tissue derived RNAs. Three of twenty-three (13%) tumor specimens showed reduced expression in tumors. One of the patients did not exhibit any change. Expression of housekeeping genes, cytokeratin-18 (FIG. 3) and glyceraldehyde-3-phosphate dehydrogenase (GAPDH) (data not shown) remained constant in tumor and normal specimens of all the patients (FIG. 3). These results were further confirmed by another set of PCGEM1 specific primers (Sense Primer 3 (SEQ ID NO: 7): 5' TGGCAACAG-GCAAGCAGAG 3' and Antisense Primer 2 (SEQ ID NO: 6): 5' GGCCAAAATAAAACCAAACAT 3'). Four of 16 (25%) patients did not exhibit detectable PCGEM1 expression in either normal or tumor tissue derived RNAs. Two of 16 (12.5%) tumor specimens showed reduced expression in tumors. These results of PCGEM1 expression in tumor tissues could be explained by the expected individual variations between tumors of different patients. Most importantly, initial DD observations were confirmed by showing that 45% of patients analyzed did exhibit over expression of PCGEM1 in tumor prostate tissues when compared to corresponding normal prostate tissue of the same individual.

EXAMPLE 5
In situ Hybridization

In situ hybridization was performed essentially as described by Wilkinson and Green (48). Briefly, OCT embedded tissue slides stored at −80° C. were fixed in 4% PFA (paraformaldehyde), digested with proteinase K and then again fixed in 4% PFA. After washing in PBS, sections were treated with 0.25% acetic anhydride in 0.1 M triethanolamine, washed again in PBS, and dehydrated in a graded ethanol series. Sections were hybridized with $^{35}$S-labeled riboprobes at 52° C. overnight. After washing and RNase A treatment, sections were dehydrated, dipped into NTB-2 emulsion and exposed for 11 days at 4° C. After development, slides were lightly stained with hematoxylin and mounted for microscopy. In each section, PCGEM1 expression was scored as percentage of cells showing $^{35}$S signal: 1+, 1–25%; 2+, 25–50%; 3+, 50–75%, 4+, 75–100%.

Figure 17:
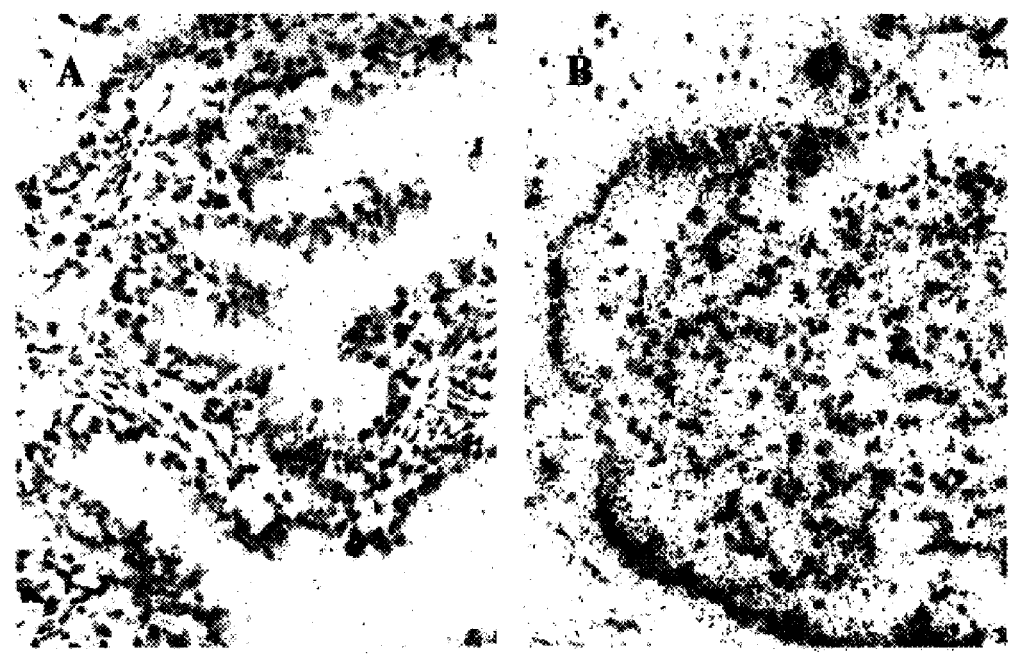
FIG. 17 depicts a representative example of in situ hybridization results showing PCGEM1 expression in normal and tumor areas of prostate cancer tissues.

Paired normal (benign) and tumor specimens from 13 patients were tested using in situ hybridization. A representative example is shown in FIG. 17. In 11 cases (84%) tumor associated elevation of PCGEM1 expression was detected. In 5 of these 11 patients the expression of PCGEM1 increased to 1+ in the tumor area from an essentially undetectable level in the normal area (on the 0 to 4+ scale). Tumor specimens from 4 of 11 patients scored between 2+ (example shown in FIG. 17B) and 4+. Two of 11 patients showed focal signals with 3+ score in the tumor area, and one of these patients had similar focal signal (2+) in an area pathologically designated as benign. In the remaining 2 of the 13 cases there was no detectable signal in any of the tissue areas tested. The results indicate that PCGEM1 expression appears to be restricted to glandular epithelial cells. (FIG. 17 shows an example of in situ hybridization of $^{35}$S labeled PCGEM1 riboprobe to matched normal (A) versus tumor (B) sections of prostate cancer patients. The light gray areas are hematoxylin stained cell bodies, the black dots represent the PCGEM1 expression signal. The signal is background level in the normal (A), 2+ level in the tumor (B) section. The magnification is 40x.)

EXAMPLE 6
PCGEM1 Gene Expression in Prostate Tumor Cell Lines

PCGEM1 gene expression was also evaluated in established prostate cancer cell lines: LNCaP, DU145, PC3 (all from ATCC), DuPro (available from Dr. David Paulson, Duke University, Durham, N.C.), and an E6/E7—immortalized primary prostate cancer cell line, CPDR1 (47). CPDR1 is a primary CaP derived cell line immortalized by retroviral vector, LXSN 16 E6 E7, expressing E6 and E7 gene of the human papilloma virus 16. LNCaP is a well studied, androgen-responsive prostate cancer cell line, whereas DU145, PC3, DuPro and CPDR1 are androgen-independent and lack detectable expression of the androgen receptor. Utilizing the RT-PCR assay described above, PCGEM1 expression was easily detectable in LNCaP (FIG.

4). However, PCGEM1 expression was not detected in prostate cancer cell lines DU145, PC3, DuPro and CPDR. Thus, PCGEM1 was expressed in the androgen-responsive cell line but not in the androgen-independent cell lines. These results indicate that hormones, particularly androgen, may play a key role in regulating PCGEM1 expression in prostate cancer cells. In addition, the results suggest that PCGEM1 expression may be used to distinguish between hormone responsive tumor cells and more aggressive hormone refractory tumor cells.

To test if PCGEM1 expression is regulated by androgens, we performed experiments evaluating PCGEM1 expression in LNCaP cells (ATCC) cultured with and without androgens. Total RNA from LNCaP cells, treated with synthetic androgen R1881 obtained from (DUPONT, Boston, Mass.), were analyzed for PCGEM1 expression. Both RT-PCR analysis (FIG. 5a) and Northern blot analysis (FIG. 5b) were conducted as follows.

Figure 5A:
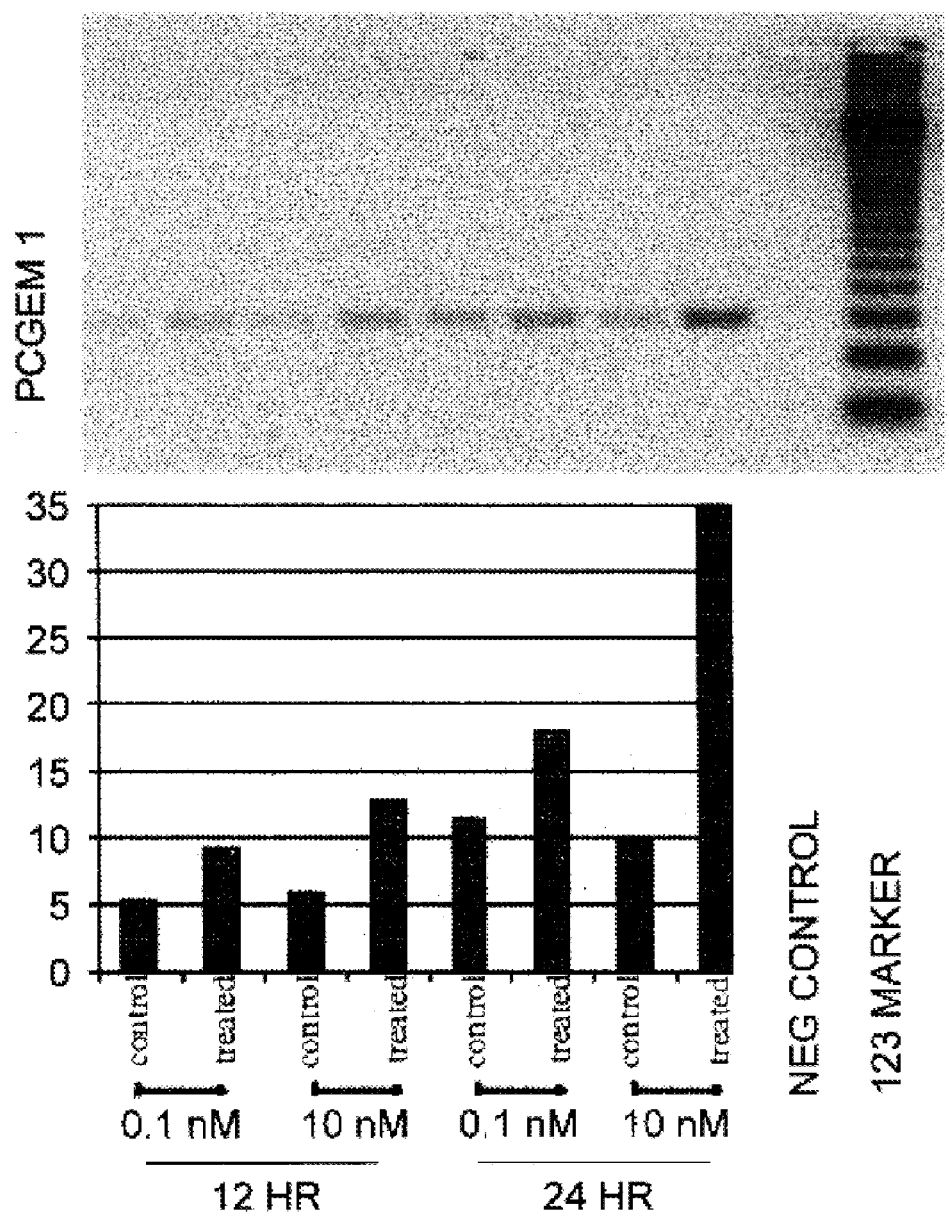
FIG. 5a depicts the androgen regulation of PCGEM1 expression in LNCaP cells, as measured by reverse transcriptase PCR.

LNCaP cells were maintained in RPMI 1640 (Life Technologies, Inc., Gaithersburg, Md.) supplemented with 10% fetal bovine serum (FB S, Life Technologies, Inc., Gaithersburg, Md.) and experiments were performed on cells between passages 20 and 35. For the studies of NKX3.1 gene expression regulation, charcoal/dextran stripped androgen-free FBS (cFBS, Gemini Bio-Products, Inc., Calabasas, Calif.) was used. LNCaP cells were cultured first in RPMI 1640 with 10% cFBS for 4 days and then stimulated with a non-metabolizable androgen analog R1881 (DUPONT, Boston, Mass.) at different concentrations for different times as shown in FIG. 5A. LNCaP cells identically treated but without R1881 served as control. Poly A+ RNA derived from cells treated with/without R1881 was extracted at indicated time points with RNAzol B (Tel-Test, Inc, Tex.) and fractionated (2 $\mu$g/lane) by running on 1% formaldehyde-agarose gel and transferred to nylon membrane. Northern blots were analyzed for the expression of PCGEM1 using the nucleic acid molecule set forth in SEQ ID NO: 4 as a probe. The RNA from LNCaP cells treated with R1881 and RNA from control LNCaP cells were also analyzed by RT-PCR assays as described in Example 4.

Figure 5B:
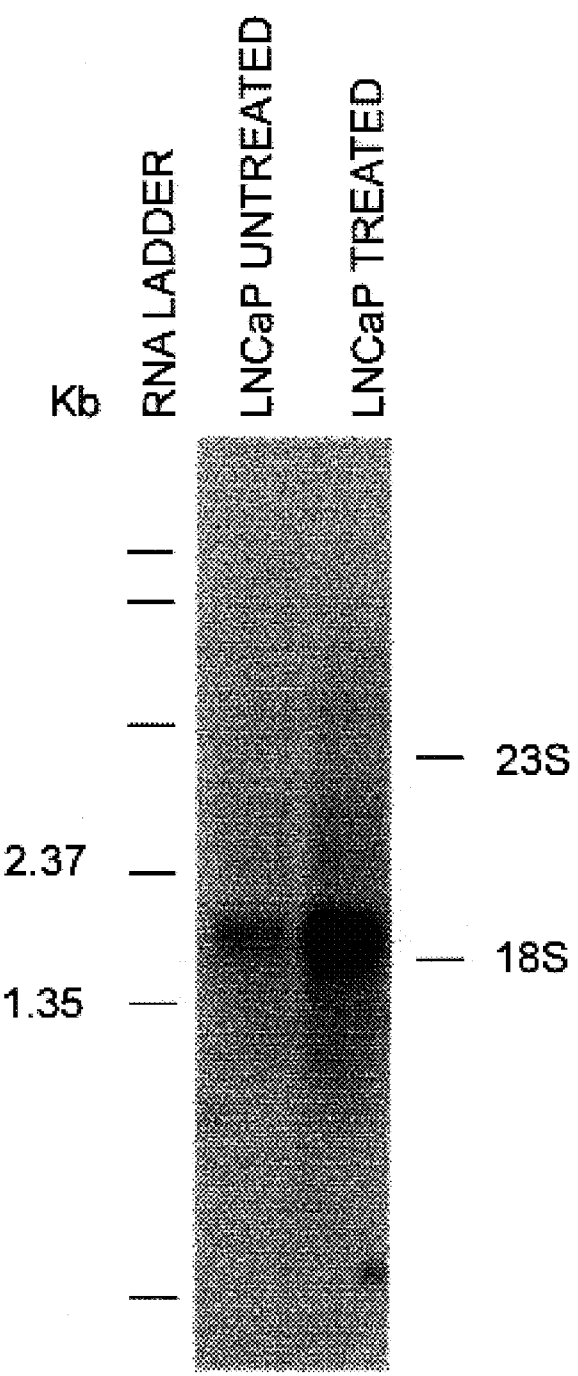
FIG. 5b depicts the androgen regulation of PCGEM1 expression in LNCaP cells, as measured by Northern blot hybridization.

As set forth in FIGS. 5a and 5b, PCGEM1 expression increases in response to androgen treatment. This finding further supports the hypothesis that the PCGEM1 expression is regulated by androgens in prostate cancer cells.

EXAMPLE 7
Tissue Specificity of PCGEM1 Expression

Figure 6A:
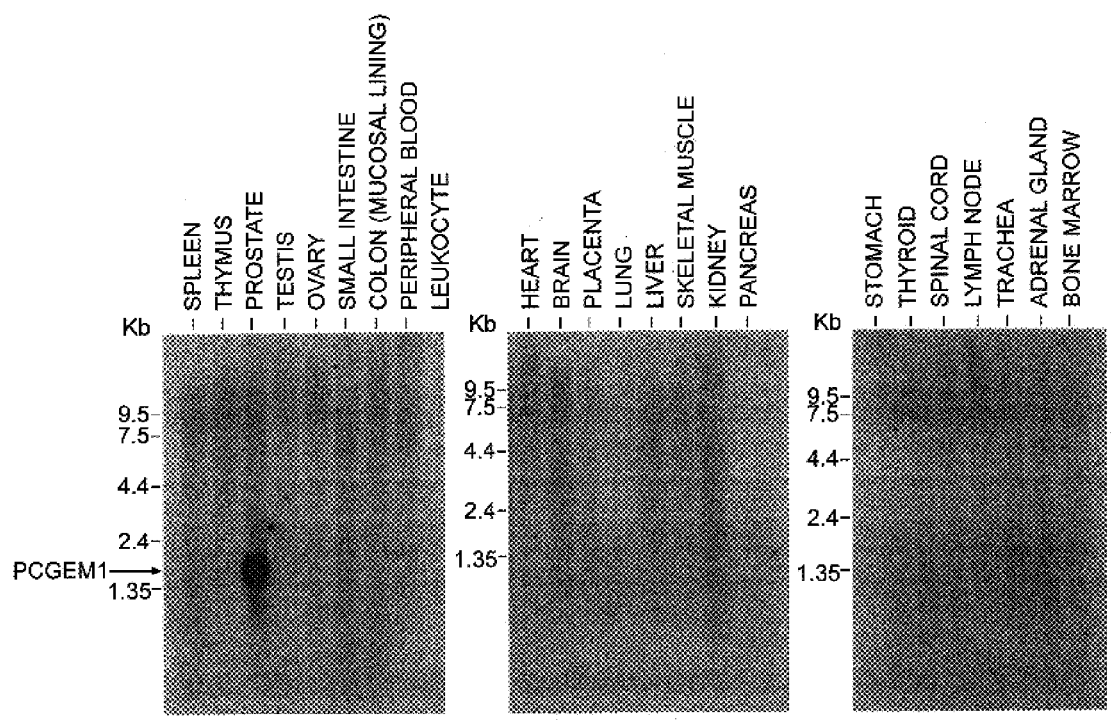
FIG. 6a depicts the prostate tissue specific expression pattern of PCGEM1.

Multiple tissue Northern blots (CLONTECH, CA) conducted according to the manufacturer's directions revealed prostate tissue-specific expression of PCGEM1. Polyadenylate RNAs of 23 different human tissues (heart, brain, placenta, lung, liver skeletal muscle, kidney, pancreas, spleen, thymus, prostate, testis, ovary, small intestine, colon, peripheral blood, stomach, thyroid, spinal cord, lymph node, trachea, adrenal gland and bone marrow) were probed with the 530 base pair PCGEM1 cDNA fragment (nucleotides 410 to 940 of SEQ ID NO:1). A 1.7 kilobase mRNA transcript hybridized to the PCGEM1 probe in prostate tissue (FIG. 6a). Hybridization was not observed in any of the other human tissues (FIG. 6a). Two independent experiments revealed identical results.

Figure 6B:
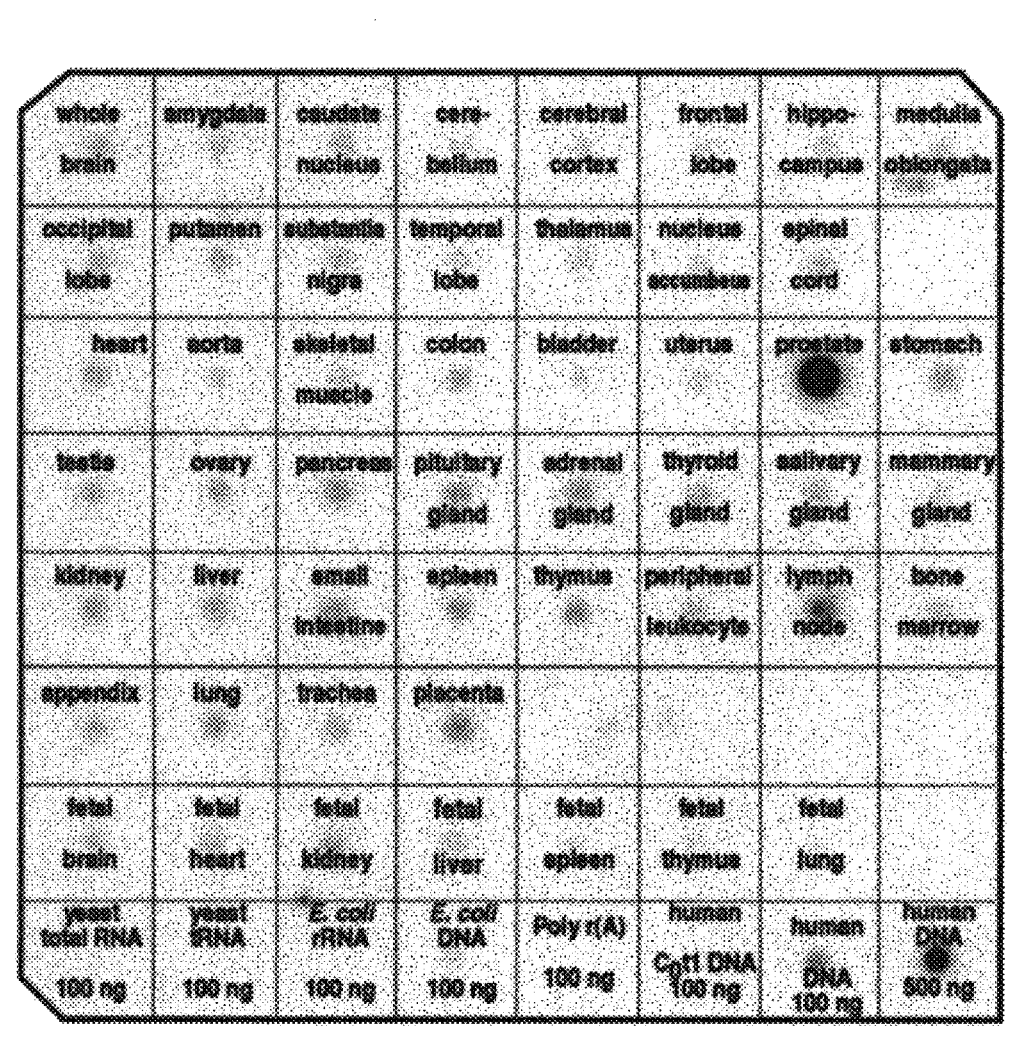

Additional Northern blot analyses on an RNA master blot (Clontech, CA) conducted according to the manufacturer's directions confirm the prostate tissue specificity of the PCGEM1 gene (FIG. 6b). Northern blot analyses reveal that the prostate tissue specificity of PCGEM1 is comparable to the well known prostate marker PSA (77mer oligo probe) and far better than two other prostate specific genes PSMA (234 bp fragment from PCR product) and NKX3.1 (210 bp cDNA). For instance, PSMA is expressed in the brain (37) and in the duodenal mucosa and a subset of proximal renal tubules (38). While NKX3.1 exhibits high levels of expression in adult prostate, it is also expressed in lower levels in testis tissue and several other tissues (39).

EXAMPLE 8
Biologic Functions of the PCGEM1

Figure 10:
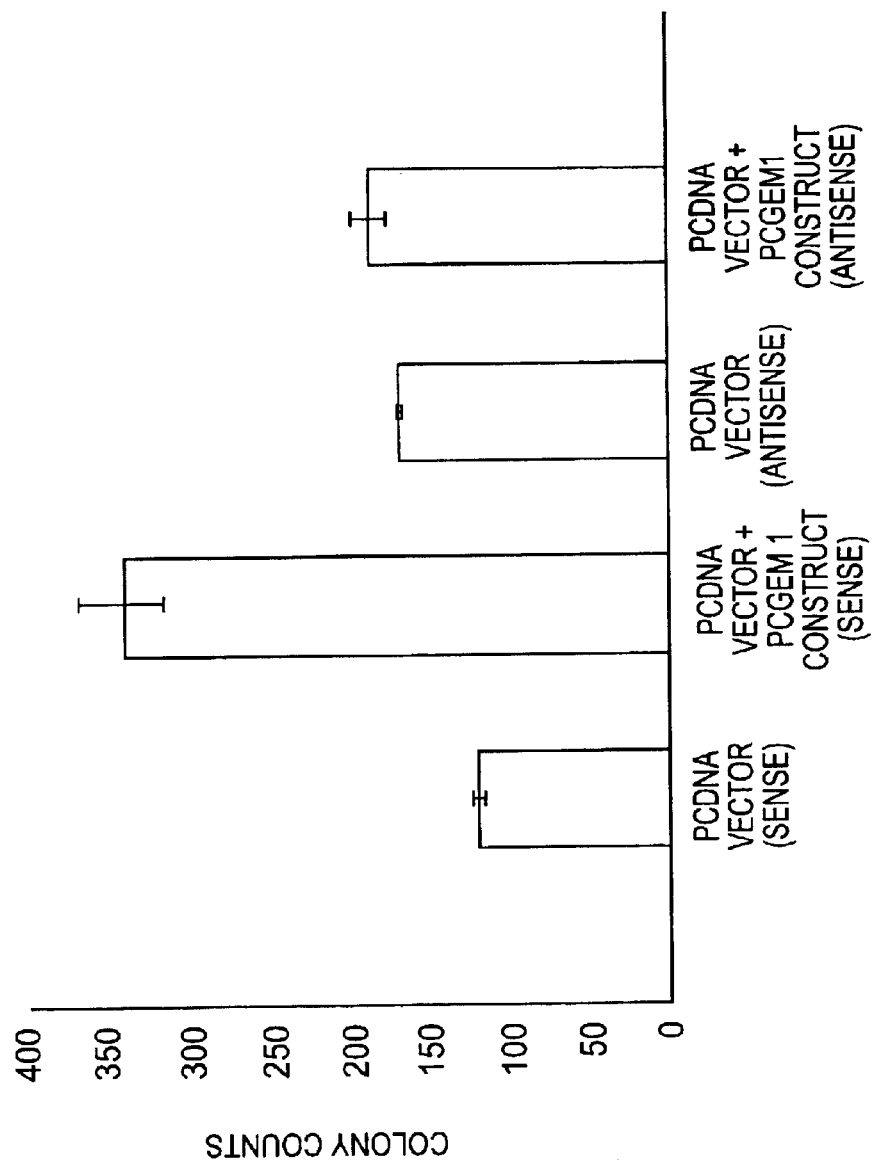
FIG. 10 depicts the colony formation of NIH3T3 cell lines expressing various PCGEM1 constructs.

The tumor associated PCGEM1 overexpression suggested that the increased expression of PCGEM1 may favor tumor cell proliferation. NIH3T3 cells have been extensively used to define cell growth promoting functions associated with a wide variety of genes (40–44). Utilizing pcDNA3.1/Hygro (+/−)(INVITROGEN, CA), PCGEM1 expression vectors were constructed in sense and anti-sense orientations and were transfected into NIH3T3 cells, and hygromycin resistant colonies were counted 2–3 weeks later. Cells transfected with PCGEM1 sense construct formed about 2 times more colonies than vector alone in three independent experiments (FIG. 10). The size of the colonies in PCGEM1 sense construct transfected cells were significantly larger. No appreciable difference was observed in the number of colonies between anti-sense PCGEM1 constructs and vector controls. These promising results document a cell growth promoting/cell survival function(s) associated with PCGEM1.

Figure 16A:
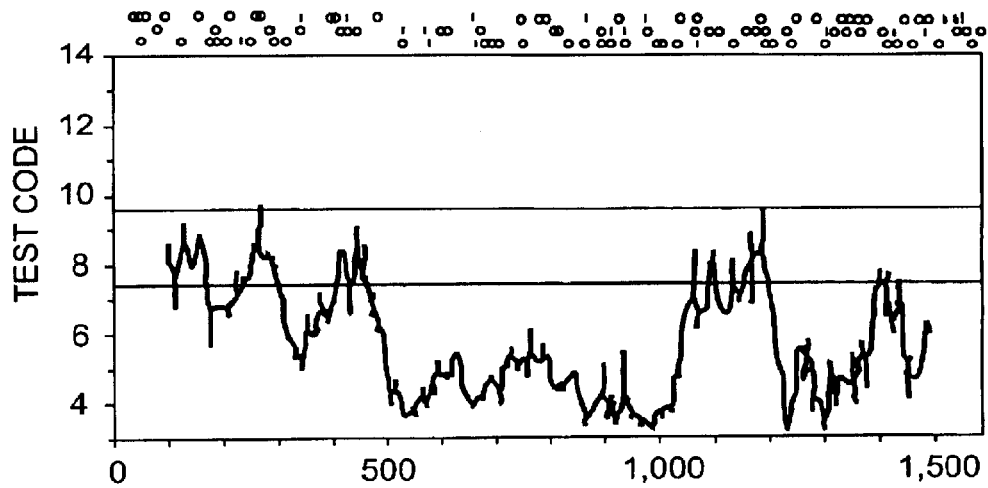
FIG. 16 depicts a graph of the hypothetical coding capacity of PCGEM1.
Figure 16B:
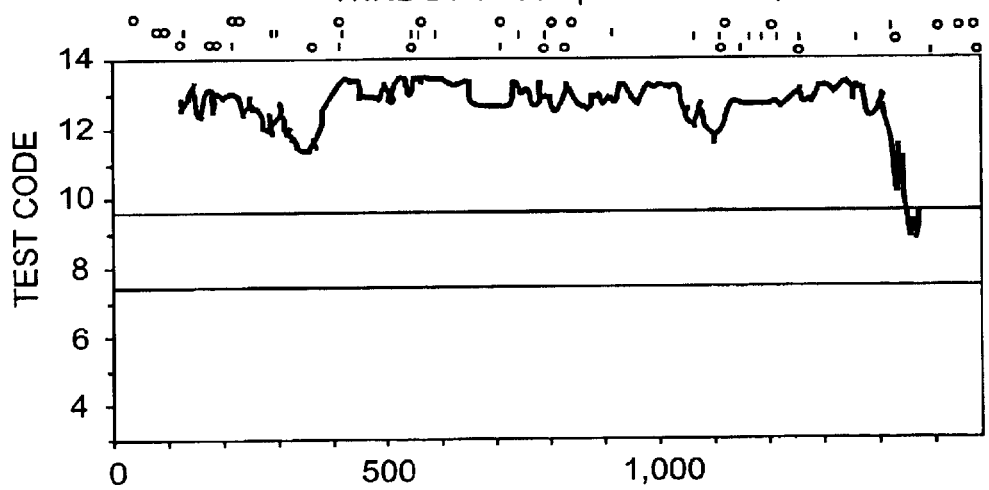

The function of PCGEM1, however, does not appear to be due to protein expression. To assess this hypothesis, we used the TestCode program (GCG Wisconsin Package, Madison, Wis.), which identifies potential protein coding sequences of longer than 200 bases by measuring the non-randomness of the composition at every third base, independently from the reading frames. Analysis of the PCGEM1 cDNA sequence revealed that, at greater than 95% confidence level, the sequence does not contain any region with protein coding capacity (FIG. 16A). Similar results were obtained when various published non-coding RNA sequences were analyzed with the TestCode program (data not shown), while known protein coding regions of similar size i.e., alpha actin (FIG. 16B) can be detected with high fidelity. (In FIG. 16, evaluation of the coding capacity of the PCGEM1 (A) and the human alpha actin (B), is performed independently from the reading frame, by using the TestCode program. The number of base pairs is indicated on the X-axis, the TestCode values are shown on the Y-axis. Regions of longer than 200 base pairs above the upper line (at 9.5 value) are considered coding, under the lower line (at 7.3 value) are considered non-coding, at a confidence level greater than 95%.)

The Codon Preference program (GCG Wisconsin Package, Madison, Wis.), which locates protein coding regions in a reading frame specific manner further suggested the absence of protein coding capacity in the PCGEM1 gene. In vitro transcription/translation of PCGEM1 cDNA did not produce a detectable protein/peptide. Although we can not unequivocally rule out the possibility that PCGEM1 codes for a short unstable peptide, at this time both experimental and computational approaches strongly suggest that PCGEM1 cDNA does not have protein coding capacity. (It should be recognized that conclusions regarding the role of PCGEM1 are speculative in nature, and should not be considered limiting in any way.

The most intriguing aspect of PCGEM1 characterization has been its apparent lack of protein coding capacity. Although we have not completely ruled out the possibility that PCGEM1 codes for a short unstable peptide, careful sequencing of PCGEM1 cDNA and genomic clones, computational analysis of PCGEM1 sequence, and in vitro transcription/translation experiments (data not shown) strongly suggest a non-coding nature of PCGEM1. It is interesting to note that an emerging group of novel mRNA-like non-coding RNAs are being discovered whose function and mechanisms of action remain poorly understood (49). Such RNA molecules have also been termed as "RNA riboregulators" because of their function(s) in development, differentiation, DNA damage, heat shock responses and tumorigenesis (40–42, 50). In the context of tumorigenesis, the H19, His-1 and Bic genes code for functional non-coding mRNAs (50). In addition, a recently reported prostate cancer associated gene, DD3 also appears to exhibit a tissue specific non-coding mRNA (51). In this regard it is important to point out that PCGEM1 and DD3 may represent a new class of prostate specific genes. The recent discovery of a steroid receptor co-activator as an mRNA, lacking protein coding capacity further emphasizes the role of RNA riboregulators in critical biochemical function(s) (52). Our preliminary results showed that PCGEM1 expression in NIH3T3 cells caused a significant increase in the size of colonies in a colony forming assay and suggests that PCGEM1 cDNA confers cell proliferation and/or cell survival function(s). Elevated expression of PCGEM1 in prostate cancer cells may represent a gain in function favoring tumor cell proliferation/survival. On the basis of our first characterization of PCGEM1 gene, we propose that PCGEM1 belongs to a novel class of prostate tissue specific genes with potential functions in prostate cell biology and the tumorigenesis of the prostate gland.

In summary, utilizing surgical specimens and rapid differential display technology, we have identified candidate genes of interest with differential expression profile in prostate cancer specimens. In particular, we have identified a novel nucleotide sequence, PCGEM1, with no match in the publicly available DNA databases (except for the homology shown in the high throughput genome sequence database, discussed above). A PCGEM1 cDNA fragment detected a 1.7 kb mRNA on Northern blots with selective expression in prostate tissue. Furthermore, this gene was found to be up-regulated by the synthetic androgen, R1881. Careful analysis of microdissected matched tumor and normal tissues further revealed PCGEM1 over-expression in a significant percentage of prostate cancer specimens. Thus, we have provided a gene with broad implications for the diagnosis, prevention, and treatment of prostate cancer.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention.

REFERENCES

1. Parker S L, Tong T, Bolden S, and Wingo P A: Cancer statistics. *CA Cancer J. Clin.,* 46:5–27, 1996.
2. Visakorpi T, Kallioniemi O P, Koivula T and Isola J: New prognostic factors in prostate carcinoma. *Eur. Uro.,* 24:438–449, 1993.
3. Mostofi F K: Grading of prostate carcinoma. *Cancer Chemothera Rep.,* 59:111, 1975.
4. Lu-Yao G L, McLerran D, Wasson J, Wennberg J E: An assessment of radical prostatectomy. Time trends, Geographical Variations and Outcomes. *JAMA,* 269:2633–2636, 1993.
5. Partin A W and Oesterling J E: The clinical usefulness of prostate-specific antigen: update 1994, *J. Urol.,* 152:1358–1368, 1994.
6. Wasson J H, Cushman C C, Bruskewitz R C, Littenberg B, Mulley A G, and Wennberg J E: A structured literature review of treatment for localized CaP. *Arch. Fam. Med.,* 2:487–493, 1993.
7. Weinberg R A: How cancer arises. *Sci. Amer.,* 9, 62–70, 1996.
8. Bostwick D G: High grade prostatic intraepithelial neoplasia: The most likely precursor of prostate cancer. *Cancer,* 75:1823–1836, 1995.
9. Bostwick D G, Pacelli A, Lopez-Beltran A: Molecular Biology of Prostatic Intraepithelial Neoplasia. *The Prostate,* 29:117–134, 1996.
10. Pannek J, Partin A W: Prostate specific antigen: What's new in 1997. *Oncology,* 11:1273–1278, 1997.
11. Partin A W, Kattan M W, Subong E N, Walsh P C, Wojno K J, Oesterling J E, Scardino P T, Pearson J D: Combination of prostate specific antigen, clinical stage, and Gleason score to predict pathological stage of localized prostate cancer. A multi-institutional update. *JAMA,* 277:1445–1451, 1997.
12. Gomella L G, Raj G V, Moreno J G: Reverse transcriptase polymerase chain reaction for prostate specific antigen in management of prostate cancer. *J. Urol.,* 158:326–337, 1997.
13. Gao C L, Dean R C, Pinto A, Mooneyhan R, Connelly R R, McLeod D G, Srivastava, S, Moul J W: Detection of PSA-expressing prostatic cells in bone marrow of radical prostatectomy patients by sensitive reverse transcriptase-polymerase chain reaction (RT-PCR). 1998 International Symposium on Biology of Prostate growth, National Institutes of Health, p. 83, 1998.
14. Garnick M B, Fair W R: Prostate cancer. Sci. Amer., 75–83, 1998.
15. Moul J W, Gaddipati J, and Srivastava S: 1994. Molecular biology of CaP. Oncogenes and tumor suppressor genes. *Current Clinical Oncology:* CaP. (Eds. Dawson, N. A. and Vogelzang, N. J.), Wiley-Liss Publications, 19–46.
16. Lalani E-N, Laniado M E and Abel P D: Molecular and cellular biology of prostate cancer. *Cancer and Mets. Rev.* 16:29–66, 1997.
17. Shi X B, Gumerlock P H, deVere White R W: Molecular Biology of CaP *World J. Urol;* 14, 318–328, 1996.
18. Heidenberg H B, Bauer J J, McLeod D G, Moul J W and Srivastava S: The role of p53 tumor suppressor gene in CaP: a possible biomarker? *Urology,* 48:971–979, 1996.
19. Bova G S and Issacs W B: Review of allelic loss and gain in prostate cancer. *World J. Urol.,* 14:338–346, 1996.
20. Issacs W B and Bova G S: Prostate Cancer: *The Genetic Basis of Human Cancer.* Eds. Vogelstein B, and Kinzier K W, McGraw-Hill Companies, Inc., pp. 653–660, 1998.
21. Srivastava S and Moul J W: Molecular Progression of Prostate Cancer. *Advances in Oncobiology.* (In Press) 1998.
22. Sakr W A, Macoska J A, Benson P, Benson D J, Wolman S R, Pontes J E, and Crissman: Allelic loss in locally metastatic, multi-sampled prostate cancer. *Cancer Res.,* 54:3273–3277, 1994.
23. Mirchandani D, Zheng J, Miller G L, Ghosh A K, Shibata D K, Cote R J and Roy-Burman P: Heterogeneity in intratumor distribution of p53 mutations in human prostate cancer. *Am. J. Path.* 147:92–101, 1995.
24. Bauer J J, Moul J W, and McLeod D G: CaP: Diagnosis, treatment, and experience at one tertiary medical center, 1989–1994. *Military Medicine,* 161:646–653,1996.
25. Bauer J J, Connelly R R, Sesterhenn I A, Bettencourt M C, McLeod D G, Srivastava S, Moul J W: Biostatistical modeling using traditional variables and genetic biomarkers predicting the risk of prostate cancer recurrence after radical prostatectomy. *Cancer,* 79:952–962, 1997.
26. Bauer J J, Connelly R R, Sesterhenn I A, DeAusen J D, McLeod D G, Srivastava S, Moul J W: Biostatistical modeling using traditional preoperative and pathological prognostic variables in the selection of men at high risk of disease recurrence after radical prostatectomy. *J. Urol.,* 159(3):929–933, 1998
27. Sager R: Expression genetics in cancer: Shifting the focus from DNA to RNA. *Proc Natl. Acad. Sci. USA,* 94:952–957, 1997
28. Strausberg R L, Dahl C A, and Klausner R D: New opportunities for uncovering the molecular basis of cancer. *Nature Genetics,* 15:415–16, 1997.
29. Liang, Peng, and Pardec A B: Differential display of eukaryotic messenger RNA by means of the polymerase chain reaction. *Science* 257:967–971, 1992.
30. Velculescu V E, Zhang L, Vogelstein B, and Kinzler K W: Serial analysis of gene expression. *Science,* 270:484–487, 1995.
31. Chena M, Shalon D S, Davis R W, and Brown P O: Quantitative monitoring of gene expression patterns with a complementary DNA microarrays. *Science,* 270:467–470, 1995.
32. Liu A Y, Corey E, Vessella R L, Lange P H, True L D, Huang G M, Nelson P S and Hood L: Identification of differentially expressed prostate genes: Increased expression of transcription factor ETS-2 in prostate cancer. *The Prostate* 30:145–153, 1997.
33. Chuaqui R F, Englert C R, Strup S E, Vocke C D, Zhuang Z, Duray P H, Bostwick D G, Linehan W M, Liotta L A and Emmert-Buck M R: Identification of a novel transcript up-regulated in a clinically aggressive prostate carcinoma. *Urology,* 50:302–307, 1997.
34. Thigpen A E, Cala K M, Guileyardo J M, Molberg K H, McConnell J D, and Russell D W: Increased expression of early growth response-1 messenger ribonucleic acid in prostate adenocarcinoma. *J. Urol.,* 155:975–981, 1996.
35. Wang F L, Wang Y, Wong W K, Liu Y, Addivinola F J, Liang P, Chen L B, Kantoff P W and Pardee A B: Two differentially expressed genes in normal human prostate tissues and in carcinoma. *Cancer Res.,* 56:3634–3637, 1996.
36. Schleicher R L, Hunter S B, Zhang M, Zheng M, Tan W, Bandea C I, Fallon M T, Bostwick D G, and Varma V A: Neurofilament heavy chain-like messenger RNA and protein are present in benign prostate and down regulated in prostate carcinoma. *Cancer Res.,* 57:3532–3536, 1997.
37. O'Keefe, D S, S u, S L, Bacich D J, Horiguchi Y, Luo Y, Powell C T, Zandvliet D, Russell P J, Molloy P L, Nowak, N J, Shows, T B, Mullins, C, Vonder Haar R A, Fair W R, and Heston W D: Mapping, genomic organization and promoter analysis of the human prostate-specific membrane antigen gene. *Biochim Biophys Acta,* 1443(1–2):113–127, 1998.
38. Silver D A, Pellicer I, Fair W R, Heston, W D, and Cordon-Cardo C: Prostate-specific membrane antigen expression in normal and malignant human tissues. *Clin Cancer Res,* 3(1):81–85, 1997.
39. He W W, Sciavolino P J; Wing J, Augustus M, Hudson P, Meissner P S, Curtis R T, Shell B K, Bostwick D G, Tindall D J, Gelmann E P, Abate-Shen C, and Carter K C: A novel prostate-specific, androgen-regulated homeobox gene (NKX3.1) that maps to 8p21, a region frequently deleted in prostate cancer. Genomics 43(1):69–77, 1997.
40. Crespi M D, Jurkevitch E, Poiret M, d'Aubenton-Carafa Y, Petrovics G, Kondorosi E, and Kondorosi A: Enod 40, a gene expressed during nodule organogenesis, codes for a non-translatable RNA involved in plant growth. *The EMBO J* 13:5099–5112, 1994.
41. Velleca M A, Wallace M C and Merlie J P: A novel synapse-associated non-coding RNA. *Mol. Cell Bio.* 14:7095–7104, 1994.
42. Takeda K. Ichijoh, Fujii M, Mochida Y, Saitoh M, Nishitoh H, Sampath T K and Miyazonok: Identification of a novel bone morphogenetic protein responsive gene that may function as non-coding RNA. *J. Biol. Chem.* 273:17079–17085, 1998.
43. Van de Sande K, Pawlowski K, Czaja I, Wieneke U, et al: Modification of phytohormone response by a peptide encode by ENOD 40 of legumes and a non-legume. *Science* 273:370–373.
44. Hao Y, Crenshaw T, Moulton T, Newcomb E and Tycko B: Tumor suppressor activity of H19RNA. *Nature.* 365:764–767, 1993.
45. Neumaier M, Gerhard M, Wagener C: Diagnosis of micrometastases by the amplification of tissue specific genes. *Gene.* 159(1):43–47, 1995.
46. Gaddipati J, McLeod D, Sesterhenn I, Hussussian C, Tong Y, Seth P, Dracopoli N, Moul J and Srivastava S: Mutations of the p16 gene product are rare in prostate cancer. *The Prostate.* 30:188–194, 1997.
47. Davis L D, Sesterhenn I A, Moul J W and Srivastava S: Characterization of prostate cancer cells immortalized with E6/E7 genes. Int. Symp. On Biol. Of Prost. Growth Proceedings, National Institutes of Health., 77, 1998.
48. Wilkinson, D., & Green, J. (1990) in *Post implantation Mammalian Embryos,* eds. Copp, A. J. & Cokroft, D. L. (Oxford University Press, London), pp. 155–171.
49. Erdmann, V. A., Szymanski, M., Hochberg, A., de Groot, N., & Barciszewski, J. (1999) *Nucleic Acids Research* 27, 192–195.
50. Askew, D. S., & Xu, F. (1999) *Histol Histopatho.* 14,235–241.
51. Bussemakers, M. J. H., Van Bokhoven, A., Verhaegh, G. W., Smit, F. P., Karthaus, H. F., Schalken, J. A., Debruyne, F. M., Ru, N., & Isaacs, W. B. (1999) *Cancer Res.* 59, 5975–5979.
52. Lanz, R. B., McKenna, N. J., Onate, S. A., Albrecht, U., Wong, J., Tsai, S. Y., Tsai, M. J., & O'Mally, B. W. (1999) *Cell* 97, 17–27.
53. Srikantan V, Zou Z, Petrovics G, Xu L, Augustus M, Davis L, Livezey J R, Connell T, Sesterhenn I A, Yoshino K, Buzard G S, Mostofi F K, McLeod D G, Moul J W, and Srivastava S: PCGEM1: A Novel Prostate Specific Gene is Overexpressed in Prostate Cancer. Submitted to *Proceedings of the National Academy of Sciences.*

We claim:

1. An isolated nucleic acid molecule selected from:
   (a) the polynucleotide sequence of SEQ ID NO:1;
   (b) an isolated nucleic acid molecule that hybridizes to either strand of a denatured, double-stranded DNA comprising the nucleic acid sequence of (a) under hybridizing conditions comprising 50% formamide and 6×SSC at 42° C. with washing conditions comprising 0.5×SSC and 0.1% SDS at 60° C., wherein messenger RNA expression of the nucleic acid molecule in NIH 3T3 cells results in about a two-fold increase in the number of colonies of NIH 3T3 cells formed in a colony-forming assay; and
   (c) an isolated nucleic acid molecule that hybridizes to either strand of a denatured, double-stranded DNA comprising the nucleic acid sequence of (a) under hybridizing conditions comprising 50% formamide and 6×SSC, with washing conditions comprising 0.2×SSC and 0.1% SDS at 68° C., wherein messenger RNA expression of the nucleic acid molecule in NIH 3T3 cells results in about a two-fold increase in the number of colonies of NIH 3T3 cells formed in a colony-forming assay.

2. The isolated nucleic acid molecule according to claim 1, wherein the polynucleotide sequence comprises SEQ ID NO:1.

3. The isolated nucleic acid molecule according to claim 1, wherein the nucleic acid molecule hybridizes to either strand of a denatured, double-stranded DNA comprising the nucleic acid sequence of (a) under hybridizing conditions comprising 50% formamide and 6×SSC, with washing conditions comprising 0.2×SSC and 0.1% SDS at 68° C., wherein the messenger RNA expression of the nucleic acid molecule in NIH 3T3 cells results in about a two-fold increase in the number of colonies of NIH 3T3 cells formed in a colony-forming assay.

4. A recombinant vector that directs the expression of the nucleic acid molecule of claim 1.

5. An isolated host cell transfected or transduced with the vector of claim 4.

6. The host cell of claim 5 selected from bacterial cells, yeast cells, and animal cells.

7. An isolated nucleic acid molecule comprising the polynucleotide sequence of SEQ ID NO: 3.

8. A vector, comprising a PCGEM1 promoter sequence operatively linked to a nucleotide sequence encoding a cytotoxic protein, wherein the PCGEM1 promoter sequence is a nucleic acid molecule comprising the polynucleotide sequence of SEQ ID NO:3.

* * * * *

SEQUENCE LISTING

<160> NUMBER OF SEQ ID NOS: 22

<210> SEQ ID NO 1
<211> LENGTH: 1603
<212> TYPE: DNA
<213> ORGANISM: Homo sapiens

<400> SEQUENCE: 1

```
aaggcactct ggcacccagt tttggaactg cagttttaaa agtcataaat tgaatgaaaa      60
tgatagcaaa ggtggaggtt tttaaagagc tatttatagg tccctggaca gcatcttttt     120
tcaattaggc agcaacctt ttgccctatg ccgtaacctg tgtctgcaac ttcctctaat      180
tgggaaatag ttaagcagat tcatagagct gaatgataaa attgtactac gagatgcact     240
gggactcaac gtgaccttat caagtgagca ggcttggtgc atttgacact tcatgatatc     300
agccaaagtg gaactaaaaa cagctcctgg aagaggacta tgacatcatc aggttgggag     360
tctccaggga cagcggaccc tttggaaaag gactagaaag tgtgaaatct attagtcttc     420
gatatgaaat tctctgtctc tgtaaaagca tttcatattt acaagacaca ggcctactcc     480
tagggcagca aaagtggca acaggcaagc agagggaaaa gagatcatga ggcatttcag     540
agtgcactgt cttttcatat atttctcaat gccgtatgtt tggttttatt ttggccaagc     600
ataacaatct gctcaagaaa aaaaaatctg gagaaaacaa aggtgccttt gccaatgtta     660
tgtttctttt tgacaagccc tgagatttct gagggaatt cacataaatg ggatcaggtc     720
attcatttac gttgtgtgca aatatgattt aaagatacaa cctttgcaga gagcatgctt     780
tcctaagggt aggcacgtgg aggactaagg gtaaagcatt cttcaagatc agttaatcaa     840
gaaaggtgct cttttgcattc tgaaatgccc ttgttgcaaa tattggttat attgattaaa     900
tttacactta atggaaacaa ccttttaactt acagatgaac aaaccccacaa agcaaaaaa    960
tcaaaagccc tacctatgat ttcatatttt ctgtgtaact ggattaaagg attcctgctt    1020
gcttttgggc ataaatgata atggaatatt tccaggtatt gtttaaaatg agggcccatc    1080
tacaaattct tagcaatact ttggataatt ctaaaattca gctggacatt gtctaattgt    1140
tttttatata catctttgct agaatttcaa atttttaagta tgtgaattta gttaattagc    1200
tgtgctgatc aattcaaaaa cattactttc ctaaatttta gactatgaag gtcataaatt    1260
caacaaatat atctcacacat acaattatag attgtttttc attataatgt cttcatctta   1320
acagaattgt ctttgtgatt gttttttagaa aactgagagt tttaattcat aattacttga   1380
tcaaaaaatt gtgggaacaa tccagcatta attgtatgtg attgttttta tgtacataag    1440
gagtcttaag cttggtgcct tgaagtcttt tgtacttagt cccatgttta aaattactac    1500
tttatatcta aagcatttat gttttttcaat tcaatttaca tgatgctaat tatggcaatt   1560
ataacaaata ttaaagattt cgaaatagaa aaaaaaaaaa aaa                       1603
```

<210> SEQ ID NO 2
<211> LENGTH: 1579
<212> TYPE: DNA
<213> ORGANISM: Homo sapiens

<400> SEQUENCE: 2

```
gcggccgcgt cgacgcaact tcctctaatt gggaaatagt taagcagatt catagagctg      60
aatgataaaa ttgtacttcg agatgcactg ggactcaacg tgaccttatc aagtgagatg     120
gagtcttgcc ctgtctccaa ggctggagcc caatggtgtg atcttggctc actgcaacct    180
```

```
ccacctccca ggttcaaacg tttctcctgc ctcagcctcc caagtaactg ggattacagc    240
aggcttggtg catttgacac ttcatgatat cagccaaagt ggaactaaaa acagctcctg    300
gaagaggact atgacatcat caggttggga gtctccaggg acagcggacc ctttggaaaa    360
ggactagaaa gtgtgaaatc tattagtctt cgatatgaaa ttctctgtct ccgtaaaagc    420
atttcatatt tacaagacac aggcctactc ctagggcagc aaaaagtggc aacaggcaag    480
cagagggaaa agagatcatg aggcatttca gagtgcactg tcttttcata tatttctcaa    540
tgccgtatgt ttggttttat tttggccaag cataacaatc tgctcaaaaa aaaaaaatct    600
ggagaaaaca aggtgccttt gccaatgtt atgtttcttt ttgacaagcc ctgagatttc    660
tgaggggaat tcacataaat gggatcaggt cattcattta cgttgtgtgc aaatatgatt    720
taaagataca accttttgcag agagcatgct ttcctaaggg taggcacgtg gaggactaag    780
ggtaaagcat tcttcaagat cagttaatca agaaaggtgc tctttgcatt ctgaaatgcc    840
cttgttgcaa atattggtta tattgattaa atttacactt aatggaaaca accttttaact    900 tacagatgaa caaaccccac aaaagcaaaa atcaaaagc cctacctatg atttcatatt    960
ttctgtgtaa ctggattaaa ggattcctgc ttgcttttgg gcataaatga taatggaata   1020
tttccaggta ttgtttaaaa tgagggccca tctacaaatt cttagcaata ctttggataa   1080
ttctaaaatt cagctggaca ttgtctaatt gtttttata tacatctttg ctagaatttc   1140 aaatttaag tatgtgaatt tagttaatta gctgtgctga tcaattcaaa aacattactt   1200
tcctaaattt tagactatga aggtcataaa ttcaacaaat atatctacac atacaattat   1260 agattgttt tcattataat gtcttcatct taacagaatt gtctttgtga ttgttttag    1320 aaaactgaga gttttaattc ataattactt gatcaaaaaa ttgtgggaac aatccagcat   1380
taattgtatg tgattgtttt tatgtacata aggagtctta agcttggtgc cttgaagtct   1440
tttgtactta gtcccatgtt taaaattact actttatatc taaagcattt atgttttca   1500 attcaattta catgatgcta attatggcaa ttataacaaa tattaaagat ttcgaaatag   1560
aaaaaaaaaa aaaaatcta                                                1579

<210> SEQ ID NO 3
<211> LENGTH: 1819
<212> TYPE: DNA
<213> ORGANISM: Homo sapiens

<400> SEQUENCE: 3
tccctcttgc gttctgcaat ttctgaaaaa aagatgttta ttgcaaagtg atatgagcac     60
tggaaaggta ctaattccaa tttgattcta attggatgag tgacatgggt aagcgattct    120
aagcatttgt gtttttttta gtagtatgga atttaattag ttctcagtat gttagtgaag    180
atgaatgaaa acatgcatat gtttccatgt attataaata ttttaaaatg caaaaaatta    240
ttctaatgaa tatataaata taaagcataa caataataat acaataccac ccataaagtc    300
atcatctaat ttaaaaacta aaacattaac acttgaatct ccccattgc aacatctttc    360 ccgacttgtg tgttttttc ttttgctttt aaaattttg tttatcata tgtctgcata    420 agattatata gctttccttg ttttaagctt tttaaataat atattgtagt tatattattt    480
gtgctttgct ttttttactt aacattatgg ttctaaaatt cagtaatgtg ttgggcatgt    540
ataatttgtt tatttttaat ctctttgaca ttcgactata taaatttcag tttgtttatt    600
gactcctttg tctatagata ctctgctatt tctgttttg ctgttacaaa aataatgctg    660
```

-continued

```
ttttaaattt cattttgtat acttttttga ggcatgtgta tgagttattc taaggtaaaa        720
aaataagaaa aaattgctgg gttataagat tgtcacatgc tcgaatttac aagataatgc        780
caaatcattt ttcaaagtaa ttatacctat ttatactacc ggtatgagta tattggtgcc        840
cacatagttg cttgttctgc caaagtttgg tatgatcgaa caataatttt tgcccatcaa        900
atggcataaa ataaaatctc agtgtgcttt taatttgcat tttctatgtt taagaattgt        960 ttcttttta accatttata atttactttt gctgaaatgc ttgcttatta tttttgctcc        1020 ccatttttc ctattggatt gcttttctca ttaatttata agaatttat atggtttaga        1080 tactaattat tatattactg aaaatacctt tatcagtttg ttgtgtactt tctactttat        1140
gtcttgtgat ggataaaagt tttaaattgt attgtgttga agttaacatt tttaaatttt        1200
ataatcagca tctttaataa tctctttmta aaattttcct ttacatagat gtcataaaga        1260
tacatctcta taatttctta ttttttggc atatgttcat taagtcattt tatcattttt        1320
tagtaataaa ttgcagttat ttatgaaaca ataattttt aaaattatat atgctttctt        1380
taaaaattga tcttagcatg cttcactatg aagcttgagg cttcactgca cgttgtactg        1440
aaattatgta taaacagtg gttctgaaaa tctctgagtt catgcaccct ttagtgtctc        1500
aggttttttt gctttgttc ttgtttttc tcacaaagca cctaagttaa ataaaaacaa        1560
agcacaaagc tatcagcttc atgtattaag tagtaagctc ccatgttaac agttgtaact        1620
tgcctggtgc ccaatagatg tcactctgtt ttcctagaaa ctttaaaata tccctcagtg        1680
ctcctgttaa ttcatggtag tgccccaagg cactctggca cccagttttg gaactgcagt        1740
tttaaaagtc ataaattgaa tgaaaatgat agcaaaggtg gaggttttta aagagctatt        1800
tataggtccc tggacagca                                                    1819

<210> SEQ ID NO 4
<211> LENGTH: 1025
<212> TYPE: DNA
<213> ORGANISM: Homo sapiens

<400> SEQUENCE: 4 tttttcaat taggcagcaa ccttttgcc ctatgccgta acctgtgtct gcaacttcct         60
ctaattggga aatagttaag cagattcata gagctgaatg ataaaattgt actacgagat       120
gcactgggac tcaacgtgac cttatcaagt gagcaggctt ggtgcatttg acacttcatg       180
atatcatcca aagtggaact aaaaacagct cctggaagag gactatgaca tcatcaggtt       240
gggagtctcc agggacagcg gaccctttgg aaaaggacta gaaagtgtga atctattag       300 tcttcgatat gaaattctct gtctctgtaa aagcatttca tatttacaag acacaggcct      360
actcctaggg cagcaaaaag tggcaacagg caagcagagg gaaaagagat catgaggcat      420
ttcagagtgc actgtctttt catatatttc tcaatgccgt atgtttggtt ttattttggc      480
caagcataac aatctgctca agaaaaaaaa atctggagaa acaaaggtg cctttgccaa       540 tgttatgttt cttttgaca agccctgaga tttctgaggg gaattcacat aaatgggatc       600
aggtcattca tttacgttgt gtgcaaatat gatttaaaga tacaacccttt gcagagagca     660 tgctttccta agggtaggca cgtggaggac taagggtaaa gcattcttca agatcagtta     720
atcaagaaag gtgctctttg cattctgaaa tgcccttgtt gcaaatattg gttatattga     780
ttaaatttac acttaatgga aacaacccttt aacttacaga tgaacaaacc cacaaaagca     840
aaaaatcaaa agccctacct atgatttcat attttctgtg taactggatt aaaggattcc     900
tgcttgcttt tgggcataaa tgataatgga atatttccag gtattgttta aaatgagggc     960
```

```
ccatctacaa attcttagca atactttgga taattctaaa attcagctgg acattgtcta      1020
attgt                                                                 1025

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:Probe/Primer

<400> SEQUENCE: 5
tgcctcagcc tcccaagtaa c                                                 21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:Probe/Primer

<400> SEQUENCE: 6
ggccaaaata aaccaaaca t                                                  21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:Probe/Primer

<400> SEQUENCE: 7
tggcaacagg caagcagag                                                    19

<210> SEQ ID NO 8
<211> LENGTH: 11801
<212> TYPE: DNA
<213> ORGANISM: Homo sapiens
<220> FEATURE:
<221> NAME/KEY: unsure
<222> LOCATION: (7470)
<223> OTHER INFORMATION: n may represent any of the four nucleotide
      bases

<400> SEQUENCE: 8
tccctcttgc gttctgcaat ttctgaaaaa aagatgttta ttgcaaagtg atatgagcac        60 tggaaggta  ctaattccaa tttgattcta attggatgag tgacatgggt aagcgattct       120
aagcatttgt gttttttta gtagtatgga atttaattag ttctcagtat gttagtgaag        180
atgaatgaaa acatgcatat gtttccatgt attataaata ttttaaaatg caaaaaatta      240
ttctaatgaa tatataaata taaagcataa caataataat acaataccac ccataaagtc      300
atcatctaat ttaaaaacta aaacattaac acttgaatct ccccattgc aacatctttc       360 ccgacttgtg tgtttttttc ttttgctttt aaaattttg ttttatcata tgtctgcata        420
agattatata gctttccttg ttttaagctt tttaaataat atattgtagt tatattattt      480
gtgctttgct tttttactt aacattatgg ttctaaaatt cagtaatgtg ttgggcatgt        540
ataatttgtt tatttttaat ctctttgaca ttcgactata taaatttcag tttgtttatt      600
gactcctttg tctatagata ctctgctatt tctgttttg ctgttacaaa ataatgctg        660 ttttaaattt catttgtat acttttttga ggcatgtgta tgagttattc taaggtaaaa       720
aaataagaaa aaattgctgg gttataagat tgtcacatgc tcgaatttac aagataatgc     780
```

```
caaatcattt ttcaaagtaa ttatacctat ttatactacc ggtatgagta tattggtgcc    840
cacatagttg cttgttctgc caaagtttgg tatgatcgaa caataatttt tgcccatcaa    900
atggcataaa ataaaatctc agtgtgcttt taatttgcat tttctatgtt taagaattgt    960
ttctttttta accatttata atttactttt gctgaaatgc ttgcttatta tttttgctcc   1020
ccattttttc ctattggatt gcttttctca ttaatttata agaattttat atggtttaga   1080
tactaattat tatattactg aaaataccTt tatcagtttg ttgtgtactt tctactttat   1140
gtcttgtgat ggataaaagt tttaaattgt attgtgttga agttaacatt tttaaatttt   1200
ataatcagca tctttaataa tctctttata aaattttcct ttacatagat gtcataaaga   1260
tacatctcta taatttctta ttttttttggc atatgttcat taagtcattt tatcattttt   1320
tagtaataaa ttgcagttat ttatgaaaca ataattttt aaaattatat atgctttctt    1380
taaaaattga tcttagcatg cttcactatg aagcttgagg cttcactgca cgttgtactg   1440
aaattatgta taaaacagtg gttctgaaaa tctctgagtt catgacacct ttagtgtctc   1500
aggtttttt gcttttgttc ttgttttttc tcacaaagca cctaagttaa ataaaaacaa    1560
agcacaaagc tatcagcttc atgtattaag tagtaagctc ccatgttaac agttgtaact   1620
tgcctggtgc ccaatagatg tcactctgtt ttcctagaaa cttaaaaata tccctcagtg   1680
ctcctgttaa ttcatggtag tgccccaagg cactctggca cccagttttg gaactgcagt   1740
tttaaaagtc ataaattgaa tgaaaatgat agcaaaggtg gaggtttta aagagctatt    1800
tataggtccc tggacagcat ctttttttcaa ttaggcagca accttttgc ctatgccgta    1860
actgtgtctg cacttcctct aattggggtg agtaagagat tttgttatgt atataatagc   1920
taagaatata gtaataatgg cttaaatcat ggttattttt aaactactaa catttagaag   1980
acaaaataaa aatgctttga aaagtataga ggttttagtg taattagcag ggaataatga   2040
aatgatttga tagggctact cagttttgta aactttggt gctttaagtc tgaatgcaga    2100
gcatggatgt tgtgatccag cctttatatg ttttccctga agaagattta atttatttgg   2160
cctttttgaga aacacatttg gcattgtaat atgttttgct tccaggttct atctccaagg   2220
ataatttgac aaaatcacac ataaatttat tttcagggca cacagtttcc cttttaggga   2280
actcacagag gtagagagta atacaataat cacatttgaa tattcagtaa gtgaggtcct   2340
catagatctt atgtgtatgt caccatgtat ataattttgt taatcactag atgtatgaga   2400
caagaaattt gaggaatctt aactagagat taaaatcagg gatttaaatc aaagaaacat   2460
ttaaatgcct cctttattat ttaaatacct gcatgggaga atcattgaaa aaaaaataaa   2520
aagcatacaa cttgggaata ttataaacca agaagaattt gttattctgg ttgattttt    2580
tttcaggctc cgcacaggca acttaccttt atctctttgt gattttttatt tcttgttaaa   2640
atatacagaa atagttaagc agattcatag agctgaatat aaaatttact acgagatgca   2700
ctgggactca acgtgacctt atcaagtgac ttatcagtga ggtgagcatt cttaattcag   2760
ataatggaac ttattatcat aatcttttgc ttatgctatt gttgagctta actacttatt   2820
catatttgca tatgcatatt gagataatat catttcatta atttcagtac tgaacactaa   2880
tctcctaaga gtaattgtga agtttcaga ttgcactatt tttaactata tatctgtatg     2940
ttatcttcat atatgcttga ataacttata agcaattgaa actttcaatt acagtatact   3000
attgaagcaa atcaactaat atatacacat atccattagc aatagtagat aattttgta    3060
aatgtccagc acagttcttc atatgtagag gatgttcaaa ttggctaagt tcctttttctc   3120
```

-continued

```
tcttaattat tagtattttt cctactgctc tttgtataat tattccttcc tctttagctc    3180
caatccttac aatctattct taacatagca actgggaaga aagtttttaa acataaacca    3240
gatgatgtca ctccacccca caaaacttcc actattctct gtcacacata gaaagaaaga    3300
aaaaaaatat tgaaaaccta caaagacttg ctatgatctg gtccaggctc tccctaaaat    3360
ttcatgtaat ttccagccac taggccttttc tggctctcct tcaatctcat tagccttttc    3420
actactacaa gttagactgg gttttggccg aggtattttc tttttttcata ttttgccttt    3480
gcctagattg ctcttccaat agatattcac aattgcatca tcatttctat atacgtgcta    3540
aaaggtttcc ttgtccaaaa tagcttcagt gaccacctga tctagaatag tctcgatcaa    3600
aagtttcttt tccttttcct caccacttga tatttatatc aaacatttat ttgtgtaatt    3660
tatgtgtttg tttgttttct gtactagcat tatgatgacc atactatttg atgccccca    3720
aaaaatactt tcgagaatga cagggcaaag ctaaataat taaattatat aattttgaca    3780
taggcactat tgacaaaaag caattgatgt tatgatagtg ttagatctat gaaatagtac    3840
tatttaaaag taattctctg aaatacaatt ttctaaaact aaaagcagca tatgtacatg    3900
aaacaccaaa aaacttcctt atattatca ctggaagatt taaaatagta taagtagtaa    3960
cttatttaat atattttga ttatttaatt aattttatag tatccaactc taatataatg    4020
ccagtggtat ttgttcaaaa tattttaatg ttgtctattt attttaatt tgcctaaaaa    4080
ttatcttaaa tgaaattttt tggttaataa atttgaaaat actgaaaccc tcatctccag    4140
tctctgtgga tcctaaagtt tttagttgag aaaataattt ttctctagag aatgaagtag    4200
cttgtaagct tggagaaatt tctgctaaat aaatgatatt atcaactctt attttcttca    4260
atacgaaata tataaatatt tcagctcata tattttttgca ggtgctatgc ttttgcttcc    4320
aatcataatt tctgacaaat attttggaag tcaaaacttg tcttctattt tgttatttaa    4380
aattatatag actactttg taaacctta tactatcaaa tcataggcaa tttcagtttg    4440
atttcattct ggtgcagaat ataagtttat ccaagtaaaa caggagtcac ttcaaaagat    4500
tcctcccact gactgagata ttccaaagcc aactttgcaa aatttcagaa ttaaatatta    4560
tacttctttg taccttcatt ttatttgttc aatttttctt tgtgtttgta gaaaatttta    4620
atattttct gttttcaagt tttgattta atttactact ttataatttt taaaggtaag    4680
ttttgtgagg ctatattcat tatgtgtttt gaataaagac atacaattaa ttttgagaac    4740
tgcaataaaa attataagac tattaaaaat gcagtaagtg tactacactt aggctgctaa    4800
aaatgcagta ccagtagact acatttaggc tgcttaaagt tagttcttct aagtaccata    4860
tactttaaaa ttttagctaa tgatggagaa caaagacaga aagactgtgt taccatattc    4920
tagttggcca ttttgttttg ttttgagaga cgtcacatca gccttatcat aaaaattatt    4980
tggttttacc attttgactg tgagcaaaat atacagcata atatacaaaa taaaatatat    5040
gtacatcttc acaacttctt gtttaggatg caattatata tatatata tatatattta    5100
ttattatact ttaagttcta gggtacatgg caccacgtgc aggttgttac atatgtatac    5160
atgtgccatg ttggtgtgct gcacccatta actcgtcatt tacattaggt gtatctccta    5220
atgctatccc tccctctct ccccaccca caacaagccc cggtgtgtga tgttcccctt    5280
cctgtgtcca tgtgttctca ttgttcaatt cccacctatg agtgagaaca cgcagtgttt    5340
gcttttttgt ccttgcaata gtttgctgag aatgatggtt tccagcttca tccatgtccc    5400
tacaaaggac atgaactcat catttttat ggctgcatag tattccatgg tgtatatgtg    5460
ccaccatttt cttaatccga gtctgtccat tgttgttgga catttgggtt gcaattttga    5520
```

```
gtttcatgtg tagcatgtat agcacaacca attaagattt ctttctttct ctctttttt   5580
ttttttttg ttgaaatgga gtcttgcctg tctccaaggc tggagcccaa tggtgtgatc   5640
ttggcttact gcaacctcca cctcccgggt tcaagcgatt ctcctgcctc agccatccga   5700
gtagctggga ctataggcgt gcaccaccat gcccagctaa ttttgtatt tttagtacag   5760
acggggtttc accacggtgg ccaggatggt ctcaatttct tgacctcatg attcacccgc   5820
cttggcctcc caaagtgctg ggattacagg tgtgaaccac caagcccggc ctgtcacaag   5880
ttttagtgt tctatttaa tacagaaatt agataaatcc aaagagaaag acatttcata    5940
tgtgcgtaga gttgtcggaa gaaatgagag tcttataaat aactttaaaa attgtgaaga   6000
aataaaggca aaatagtcct atgcagtttg atttaaatat attcttaata agagctactt   6060
ttgtgaaaac cagaatattg aaacatgtag atatggatct tcattagtga ctgacataat   6120
atattgttat tgttactatt ttattgtatc agccaactaa tattgagtgc tttgtgtatc   6180
ctaagcacta tgctaaacac tgtaccagta ttacctgata taatcatatt aatatttatt   6240
atttcacttt tcatatgaaa aaattgaagc acagattaag acactccgaa atcatacctc   6300
tattgattat cagcaccagg atttgaattg aggcactctg atccagagaa gcttttgttt   6360
ccatgaaggc ttatgtttggg gaaaaataat caaattgcct gtacctcagt tgtataaata   6420
agaggttggg ttggtagatg attctggctg attcagcaga aaagaaattt attcaaagga   6480
tatcacacag ttttcataac agttaagaat acagaggaaa cagggcacca gggctaagta   6540
cagaccaaag tccaaaacca ctgccaaagt tgcagcaagg agaacagcac aaatttgctt   6600
gctgtcaccc gccactagat gcttttgttt ggagccttga acttgactta cactgccact   6660
gacatcagca ccagtgctct ctgtgtacta ggaggtggag ttggtgacgt tgctgaactc   6720
aaagcagatg tttctgctgt gaaatagata cctaatacag aacctgcttc ctcattcatt   6780
cctctcccaa atcatatgct tgtagtgtgg ctagagtttc tgtttctcct tggtccaggc   6840
agaatttatg aagcttgcta tttatcgcct taaagattag aagaatattc ataaggtatt   6900
agattgccat aaggttgaac aaatcaacat tcaacttcaa ggattcaaca ttgttttgtt   6960
ttcttttggg atacctctgc agcagttcaa atcttatttc tgcccttgga caaccaggtt   7020
tataaatatt gcagattctc cactgactgc tttgatccta tcttctatat ttatgtatac   7080
taattagcat ataataaaag attatgttac agaatctcaa aattagtaat tatgaattga   7140
gatggtgtta tacagtacac taacatccaa gagacttgtt tattccaagg aaaatattta   7200
gagatattaa atgatatttc tcatcctta gacatataca ttttttagct tacagcctgc    7260
tttaggcaag caacagactc tcaggatctg ctcctaccag ggtctgaaca tttcctccca   7320
gttttaaaga aacaaattca ataacattg taacctccag aggaaagttc aagctctttt    7380
atagtattgt ttaaacagta cagctgagga aactaaagac agagaagtta aatgccttgg   7440
cacttagtct agatttacaa taaactcctn tctacttagg acccactaac aggggctgca   7500
tttacaccaa aacctgaag gtggcccaag tcatcactga aagtagtac aagcaccgag     7560
ggaatgactt caacaggaac aagaaagcgt ggaaggagat cctagcagga agctccacaa   7620
gaagatagca tgttacgtct tgcattggat gaagcaggtt cagagagacc tagtgacagc   7680
tatctccgtc aaggtgcaga aggagagatc attgaatgta gcatttcat gcaaaaaaa     7740
aaatgttgaa gtcttggac ttcgggagtc tgtccaaact gcaggtcact cagcctacag    7800
ttgggatgaa tttcaaaaca ccagttggag ccggttgaat cttctgctc tgctgtaata   7860
```

```
ttttcagtaa acccagcgca acaacaacaa caaaacacaa aaggaggaga agcagccaag    7920
tctcttggtt tacagagtag ctcctaatac cccttgctgt ctgtctcaag tgcccaatgg    7980
gaagatagtc aaaacaatat tcacacctgt gattcatctc tctacatgca gtgtgtgtga    8040
atctttatat actgcatatt aaggatctgt ctttacagat aaaaactaaa gcattgaagg    8100
aactccttgt tttgacttat caaagtcctt aagaaaatac tagaaaatta tagccattgt    8160
ttcaaatttt agctttatat tatcacttga atgtgatga aatgtggctg atagataata    8220
attcactgat aacctacaga caattcccat cttaaaatgg accattggat tgaagaatta    8280
aataaaattg agggttttcc ttacatgttt tgtctaaaga gcgaagtaga aacaactgtt    8340
catagatctt cattgaggat tcgcatgtga agtaagtact cctaacataa acaagtggac    8400
ttatcaacca agttccataa atcatgaaca aaaatatttg tccccagaga gactattttt    8460
ccaccacatc tcttgtaata aacacagagc ccagttcagt taaaatagtt taagggtgga    8520
cggttcaggg cctgctgagt ggcactcagt aagaaaaccc agcagaacat ttacttctct    8580
ctttattcca gagcatcaat ggccaaggct ggaagatccc agaacactga acagacattt    8640
ggtctcttat ggcctgccaa ttttcacagt gggttccaac gctttgggtc aaaccaaaat    8700
agacctgtta gaaaaatgtc ggttggaata cgctaacaat aagacagaat aaatgtgatt    8760
atttcacctc attttatag gacttgagta attttattat aacattcttg agggctggaa    8820
aatctgaatg ttaggacacc aaatatctcc agaaaacaag ttttatattt ctaatcctgc    8880
ataataaacc tggggccact gcaggcctca ttaataaaaa cctaatggta taacaataat    8940
gaggaggaaa tgccaatgcc gcacaaatct gttgagacta aaatatttct cacccccagca   9000 ggcttggtgc atttgacact tcatgatatc agccaaagtg gaactaaaaa cagctcctgg    9060
aagaggacta tgacatcatc aggttgggag tctccaggga cagcggaccc tttggaaaag    9120
gactagaaag tgtgaaatct attagtcttc gatatgaaat tctctgtctc tgtcaaaagc    9180
atttcatatt tacaagacac aggcctactc ctagggcagc aaaaagtggc aacaggcaag    9240
cagagggaaa agagatcatg aggcatttca gagtgcactg tcttttcata tatttctcaa    9300
tgccgtatgt ttggttttat tttggccaag cataacaatc tgctcaagaa aaaaaaatct    9360
ggagaaaaca aaggtgcctt tgccaatgtt atgtttcttt ttgacaagcc ctgagatttc    9420 tgagggaat tcacataaat gggatcaggt cattcattta cgttgtgtgc aaatatgatt     9480
taaagataca accttgcag agagcatgct ttcctaaggg taggcacgtg gaggactaag    9540
ggtaaagcat tcttcaagaa tcagttaatc aaagaaaggt gctctttgca ttctgaaatg    9600
cccttgttgc aaatattggt tatattgatt aaatttacac ttaatggaaa caacctttaa    9660
cttacagatg aacaaaccca caaaagcaaa aaatcaaaag ccctacctat gatttcatat    9720
tttctgtgta actggattaa aggattcctg cttgcttttg ggcataaatg ataatggaat    9780
atttccaggt attgtttaaa atgagggccc atctacaaat tcttagcaat actttggata    9840
attctaaaat tcagctggac attgtctaat tgttttttat atacatcttt gctagaattt    9900
caaattttaa gtatgtgaat ttagttaatt agctgtgctg atcaattcaa aaacattact    9960
ttcctaaatt ttagactatg aaggtcataa attcaacaaa tatatctaca catacaatta   10020
tagattgttt tcattataa tgtcttcatc ttaacagaat tgtctttgtg attgttttta    10080
gaaaactgag agtttaatt cataattacg ttgatcaaaa aattgtggga acaatccagc    10140
attaattgta tgtgattgtt tttatgtaca taaggagtct taagcttggt gccttgaagt    10200
cttttgtact tagtcccatg tttaaaatta ctactttata tctaaagcat ttatgttttt    10260
```

```
caattcaatt tacatgatgc taattatggc aattataaca atatttaaag atttcgaaat    10320
agaatatgtg aattgttcac catacataga aatgaaaagt tcatttcgta aagcaagatg    10380
ctgggtgaaa gagtgctttt gattgaaaga tcactagatt agtagagggc aagactttta    10440
gtccctaatc taccctaat agccatgtgg tcacgtgtaa gtcagtgaac ccatctcatt    10500
ctcctcatac tttttcatc tctaaaatga gggtataatt taagctcgtt catttttttt    10560 ttttttgag atagagtttt gctcttgtca cccaggttgg agtgcaatgg cacgatctca    10620
gctcactgca accctctgct tcctcggttc aagtgattct ccctgcttca gcctcccaag    10680
tgagcccggg attacaggtg cccgccacca catctgggcc tagattttt gtattttcac    10740 catgttggcc aggctggtct cgaacccta cctcaggtga tccctcgcct cggcctctca    10800
aagtgctggg attacaggtg tgagccacca cgcccagccc aatatcagtt tttctttttt    10860
aacacaaggc taacacaatc aaaatactag ctaggggaga aaaaaaaat aaggcactgt    10920 ttatgtgtaa caggctcttg ttgcaatcca ctggggcaga ccaaataaac agtaagaatc    10980
aaatcctttt catataatcc tttctttgca gaatacataa aatccccaca aatggcttat    11040 cttcctttt atgatatgtt ggagaattgt agctaagtga cagatatttt gcttgggtgt    11100
atagaccaca aaggactgtg tcttgatgat ggtttgcata aaattatacc ttagttttta    11160
ctttgtatgt tacatgttag atttagagta tgaaaattag tagggaggat tattaacaaa    11220
gaacagggca agaggagtag aattaaacct cttctaatac ctgtgcacaa gtaggctttt    11280
cagaaactct acaaccccaa cataaactgg atagttagaa aagcacactc ccaaggaagg    11340
cggttatgtt ttgcagtttg aatcagaaga atagagctat agcaatcttc attctatagt    11400
aacattaaag agcctggttt atattatagc agtcattaag atttaaaaat ttacatcttg    11460
ccgttcttct tactcacaga ttttcgagag gtaatgtaat gatcacacga ggtgagaatc    11520
actgcctttt ataatgcgat taaatgcatg aacaaagttt ccaacaaata acagtaataa    11580
aaagaaacat gtattagcac ttaataagcc aggtgctgta cgacgtgtgt tacatgcttt    11640
caatccatga actggtaaac tggtactagt atctctattg gacatgtgag gaaaccaaat    11700
ggagttgata aacagtagag ttaaaaatta ctcttcatat attatattgc ctcaatctca    11760
cagacatctc tgctaccaaa agctatcata tctagactcg a                       11801
```

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:Probe/Primer

<400> SEQUENCE: 9
tggcaacagg caagcagag                                                 19

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:Probe/Primer

<400> SEQUENCE: 10
ggccaaaata aaccaaaca t                                               21

<210> SEQ ID NO 11

```
<211> LENGTH: 24
<212> TYPE: DNA
<213> ORGANISM: Artificial Sequence
<220> FEATURE:
<223> OTHER INFORMATION: Description of Artificial Sequence:Probe/Primer

<400> SEQUENCE: 11
gcaaatatga tttaaagata caac                                      24

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:Probe/Primer

<400> SEQUENCE: 12
ggttgtatct ttaaatcata tttgc                                     25

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:Probe/Primer

<400> SEQUENCE: 13
actgtctttt catatatttc tcaatgc                                   27

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Probe/Primer

<400> SEQUENCE: 14
aagtagtaat tttaaacatg ggac                                      24

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:Probe/Primer

<400> SEQUENCE: 15
tttttcaatt aggcagcaac c                                         21

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:Probe/Primer

<400> SEQUENCE: 16
gaattgtctt tgtgattgtt tttag                                     25

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence:Probe/Primer

<400> SEQUENCE: 17
```

-continued

```
caattcacaa agacaattca gttaag                                              26

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:Probe/Primer

<400> SEQUENCE: 18
acaattagac aatgtccagc tga                                                 23

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:Probe/Primer

<400> SEQUENCE: 19
ctttggctga tatcatgaag tgtc                                                24

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:Probe/Primer

<400> SEQUENCE: 20
aaccttttgc cctatgccgt aac                                                 23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:Probe/Primer

<400> SEQUENCE: 21
gagactccca acctgatgat gt                                                  22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:Probe/Primer

<400> SEQUENCE: 22
ggtcacgttg agtcccagtg                                                     20
```